(12) United States Patent
Janssens et al.

(10) Patent No.: US 7,304,052 B2
(45) Date of Patent: Dec. 4, 2007

(54) SUBSTITUTED HOMOPIPERIDINYL BENZIMIDAZOLE ANALOGUES AS FUNDIC RELAXANTS

(75) Inventors: Frans Eduard Janssens, Beerse (BE); Jérôme Emile Georges Guillemont, Issy-les-Moulineaux (FR); François Maria Sommen, Beerse (BE)

(73) Assignee: Janssen Pharmaceuitca N.V. (BE)

( * ) Notice: Subject to any disclaimer, the term of this patent is extended or adjusted under 35 U.S.C. 154(b) by 0 days.

(21) Appl. No.: 10/169,011

(22) PCT Filed: Dec. 14, 2000

(86) PCT No.: PCT/EP00/12858

§ 371 (c)(1),
(2), (4) Date: Jun. 19, 2002

(87) PCT Pub. No.: WO01/46189

PCT Pub. Date: Jun. 28, 2001

(65) Prior Publication Data

US 2003/0139393 A1   Jul. 24, 2003

(30) Foreign Application Priority Data

Dec. 21, 1999   (EP) .................................. 99204441

(51) Int. Cl.
- *A61P 1/06* (2006.01)
- *A61K 31/55* (2006.01)
- *C07D 471/04* (2006.01)
- *C07D 403/00* (2006.01)
- *C07D 221/00* (2006.01)

(52) U.S. Cl. .......................... 514/217.05; 514/217.06; 514/217.07; 514/217.09; 514/217.1; 540/597; 540/599; 540/600; 540/603

(58) Field of Classification Search ........... 514/217.05, 514/217.06, 217.07, 217.09, 217.1; 540/597, 540/599, 600, 603
See application file for complete search history.

(56) References Cited

U.S. PATENT DOCUMENTS

| 3,781,297 A | 12/1973 | Pawellek et al. .......... 260/305 |
| 4,093,726 A | 6/1978 | Winn et al. .................. 424/250 |

FOREIGN PATENT DOCUMENTS

| DE | 2 060 197 | 6/1972 |
| EP | 0 079 545 A1 | 5/1983 |
| EP | 0 580 541 A1 | 1/1994 |
| WO | WO 01/46189 A1 | 6/2001 |

OTHER PUBLICATIONS

Orajales, Aurelio et al., *Synthesis and Structure-Activity Relationship of New Piperidinyl and Piperazinyl Derivatives as Antiallergics*, J. Heterocyclic Chem., vol. 32, May-Jun. 1995, pp. 707-718.
John J. D'Amico et al., *2-Substituted Thiobenzothiazole and Related Compounds, I. Novel Methods for the Preparation of 2,2'-Thiobis(benzothiazoles),2-(N,N-Disubstituted amino)benzothiazoles, and Related Compounds*, J. Org. Chem., vol. 30, Nov. 1965, pp. 3618-3625.
Muftic, Dr. Mahmoud, *Neue Substanzen Mit Komplementbindungshemmender Wirkung* in Vitro, Quart. J. Crude Drug Res., vol. 9, No. 3, 1969, pp. 1422-1425.
Chernova, Y. et al., *Synthesis and Biological Activity of 5,6-Dinitro Derivatives of Benzimidazole*, Khim.-Farm. ZH, vol. 25, 1991, pp. 50-52.
International Search Report (PCT), 2001.

*Primary Examiner*—Brenda Coleman
(74) *Attorney, Agent, or Firm*—Woodcock Washburn LLP

(57) ABSTRACT

The present invention relates to compounds of formula (I)

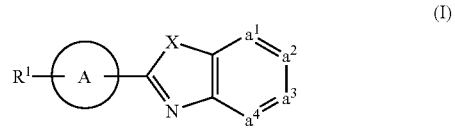

(I)

their prodrugs, N-oxides, addition salts, quaternary amines and stereochemically isomeric forms, wherein the bivalent radical -(A)- represents a saturated or an unsaturated homopiperidinyl having one double bond, and wherein said bivalent radical -(A)- is substituted with $R^2$ being hydrogen, hydroxy, $C_{1-4}$alkyl, or $C_{1-4}$alkyloxy; $-a^1=a^2-a^3=a^4$- represents an optionally substituted bivalent radical; $R^1$ is hydrogen, $C_{1-6}$alkyl, aryl$^1$, $C_{1-6}$alkyl substituted with aryl$^1$, $C_{1-4}$alkyloxycarbonyl, aryl$^1$carbonyl, aryl$^1C_{1-6}$alkylarbonyl $C_{1-4}$alkylcarbonyl, trifluoromethyl, trifluoromethylcarbonyl, $C_{1-6}$alkylsulfonyl, aryl$^1$sulfonyl, methanesulfonyl, benzenesulfonyl, trifluoromethanesulfonyl, dimethylsulfamoyl; X represents O, S or $NR^3$, wherein $R^3$ is hydrogen, $C_{1-6}$alkyl, methanesulfonyl, benzenesulfonyl, trifluoromethanesulfonyl, dimethylsulfamoyl, $C_{1-4}$alkyl substituted with aryl$^2$ and optionally with hydroxy, $C_{1-4}$alkylcarbonyl$C_{1-4}$alkyl substituted with aryl$^2$; aryl$^1$ is optionally substituted phenyl, optionally substituted pyridinyl, naphthyl, quinolinyl, or 1,3-benzodioxolyl; aryl$^2$ is optionally substituted phenyl; fundic relaxating activity. Processes for preparing said products, formulations comprising said products and their use as a medicine are disclosed, in particular for treating dyspeptic symptoms, irritable bowel syndrome and other conditions related to a hampered or impaired relaxation of the fundus.

9 Claims, No Drawings

SUBSTITUTED HOMOPIPERIDINYL BENZIMIDAZOLE ANALOGUES AS FUNDIC RELAXANTS

CROSS REFERENCE TO RELATED APPLICATIONS

This application is the national stage of application Ser. No. PCT/EP00/12858, filed Dec. 14, 2000 which application claims priority from EP 99204441.2, filed Dec. 21, 1999.

The present invention is concerned with novel compounds of formula (I) having fundic relaxating activity. The invention further relates to methods for preparing such compounds, pharmaceutical compositions comprising said compounds as well as the use as a medicine of said compounds.

EP-A-0,079,545 discloses piperazinyl substituted benzimidazole derivatives with antihistaminic acitivity.

Unexpectedly, it was found that the present novel compounds of formula (I) have fundic relaxating properties and are therefore useful to alleviate symptoms resulting from an impaired relaxation of the fundus to food ingestion.

The present invention concerns compounds of formula (I)

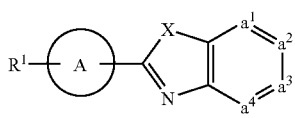

(I)

their prodrugs, N-oxides, addition salts, quaternary amines and stereochemically isomeric forms thereof, wherein

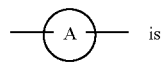 is

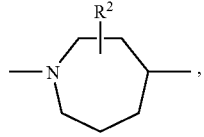 (a-1)

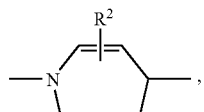 (a-2)

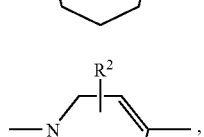 (a-3)

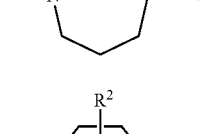 (a-4)

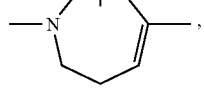 (a-4)

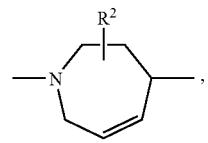 (a-5)

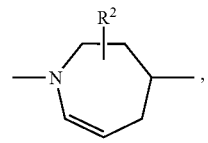 (a-6)

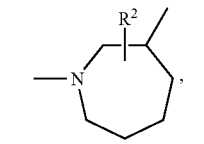 (a-7)

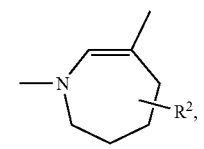 (a-8)

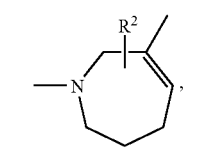 (a-9)

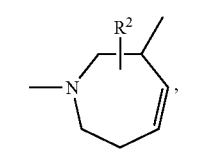 (a-10)

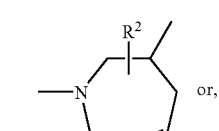 (a-11)

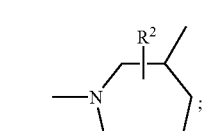 (a-12)

wherein $R^2$ is hydrogen, hydroxy, $C_{1-4}$alkyl, or $C_{1-4}$alkyloxy and when $R^2$ is hydroxy or $C_{1-4}$alkyloxy then said $R^2$ is bonded at a different position than the α-position of the ring nitrogen, or when $R^2$ is hydroxy then said $R^2$ is bonded at a different position than a vinylic position of radical (a-2), (a-3), (a-4), (a-5), (a-6), (a-8), (a-9), (a-10), (a-11), or (a-12);

-$a^1$=$a^2$-$a^3$=$a^4$- represents a bivalent radical of formula

—CH=CH—CH=CH— (b-1),

—N=CH—CH=CH— (b-2),

—CH=N—CH=CH— (b-3),

—CH=CH—N=CH— (b-4),

—CH=CH—CH=N— (b-5),

—CH=CH—N=N— (b-6),

—N=CH—CH=N— (b-7),

—N=CH—N=CH— (b-8),

—N=N—CH=CH— (b-9),

—CH=N—CH=N— (b-10), or

—CH=N—N=CH— (b-11).

wherein each hydrogen atom in the radicals (b-1) to (b-11) may optionally be replaced by halo, $C_{1-6}$alkyl, nitro, amino, hydroxy, $C_{1-6}$alkyloxy, polyhalo$C_{1-6}$alkyl, carboxyl, amino$C_{1-6}$alkyl, hydroxy$C_{1-6}$alkyl, mono- or di($C_{1-4}$alkyl)amino$C_{1-6}$alkyl, $C_{1-6}$alkyloxycarbonyl;

or wherein two hydrogen atoms on adjacent carbon atoms in the radicals (b-1) to (b-11) may optionally be replaced by —(CH$_2$)$_4$—;

$R^1$ is hydrogen, $C_{1-6}$alkyl, aryl$^1$, $C_{1-6}$alkyl substituted with aryl$^1$, $C_{1-4}$alkyloxycarbonyl, aryl$^1$carbonyl, aryl$^1$C$_{1-6}$alkylcarbonyl, aryl$^1$carbonylC$_{1-6}$alkyl, aryl$^1$oxycarbonyl, aryl$^1$C$_{1-4}$alkyloxycarbonyl, C$_{1-4}$alkylcarbonyl, trifluoromethyl, trifluoromethylcarbonyl, C$_{1-6}$alkylsulfonyl, aryl$^1$sulfonyl, methanesulfonyl, benzenesulfonyl, trifluoromethanesulfonyl, or dimethylsulfamoyl;

X represents O, S or NR$^3$, wherein R$^3$ is hydrogen; $C_{1-6}$alkyl; methanesulfonyl; benzenesulfonyl; trifluoromethanesulfonyl; dimethylsulfamoyl; aryl$^2$carbonylC$_{1-4}$alkyl; C$_{1-4}$alkyloxycarbonyl; C$_{1-4}$alkyl substituted with aryl$^2$ and optionally with hydroxy; or C$_{1-4}$alkylcarbonylC$_{1-4}$alkyl substituted with aryl$^2$;

aryl$^1$ is phenyl; phenyl substituted with 1, 2 or 3 substituents each independently selected from halo, hydroxy, $C_{1-6}$alkyl, $C_{1-6}$alkyloxy, nitro, amino, cyano, and trifluoromethyl; pyridinyl; pyridinyl substituted with 1, 2 or 3 substituents each independently selected from halo, hydroxy, $C_{1-6}$alkyl, amino, and diC$_{1-4}$alkylamino; naphthyl; quinolinyl; 1,3-benzodioxolyl; furanyl; thienyl; or benzofuranyl; and aryl$^2$ is phenyl, or phenyl substituted with 1, 2 or 3 substituents each independently selected from halo, hydroxy, $C_{1-6}$alkyl, $C_{1-6}$alkyloxy, nitro, amino, cyano, and trifluoromethyl.

In all compounds of formula (I) the substituent $R^1$ is bonded to the ring nitrogen atom of the bivalent

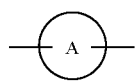

radical.

The term prodrug as used throughout this text means the pharmacologically acceptable derivatives, e.g. esters and amides, such that the resulting biotransformation product of the derivative is the active drug as defined in the compounds of formula (I). The reference by Goodman and Gilman (The Pharmacological Basis of Therapeutics, 8$^{th}$ ed., McGraw-Hill, Int. Ed. 1992, "Biotransformation of Drugs", p. 13-15) describing prodrugs generally, is hereby incorporated.

As used in the foregoing definitions halo is generic to fluoro, chloro, bromo and iodo; $C_{1-4}$alkyl defines straight and branched chain saturated hydrocarbon radicals having from 1 to 4 carbon atoms such as, for example, methyl, ethyl, propyl, butyl, 1-methyl-ethyl, 2-methylpropyl and the like; $C_{1-6}$alkyl is meant to include $C_{1-4}$alkyl and the higher homologues thereof having 5 or 6 carbon atoms, such as, for example, 2-methylbutyl, pentyl, hexyl and the like; and polyhalo$C_{1-6}$alkyl defines a polyhalosubstituted $C_{1-6}$alkyl with from one up to six halogen atoms such as, for example, difluoro- or trifluoromethyl. Hydroxy$C_{1-6}$alkyl refers to $C_{1-6}$alkyl substituted with a hydroxyl group. Amino$C_{1-6}$alkyl refers to $C_{1-6}$alkyl substituted with an amino group. The term "sulfonyl" stands for a —SO$_2$— group, and "dimethylsulfamoyl" stands for a (CH$_3$)$_2$N—SO$_2$— group.

For therapeutic use, salts of the compounds of formula (I) are those wherein the counterion is pharmaceutically acceptable. However, salts of acids and bases which are non-pharmaceutically acceptable may also find use, for example, in the preparation or purification of a pharmaceutically acceptable compound. All salts, whether pharmaceutically acceptable or not are included within the ambit of the present invention.

The pharmaceutically acceptable acid addition salts are meant to comprise the therapeutically active non-toxic acid addition salt forms which the compounds of formula (I) are able to form. The pharmaceutically acceptable acid addition salts can conveniently be obtained by treating the base form with such appropriate acid. Appropriate acids comprise, for example, inorganic acids such as hydrohalic acids, e.g. hydrochloric or hydrobromic acid, sulfuric, nitric, phosphoric and the like acids; or organic acids such as, for example, acetic, propanoic, hydroxyacetic, lactic, pyruvic, oxalic (i.e. ethanedioic), malonic, succinic (i.e. butanedioic acid), maleic, fumaric, malic, tartaric, citric, methanesulfonic, ethanesulfonic, benzenesulfonic, p-toluenesulfonic, cyclamic, salicylic, p-aminosalicylic, pamoic and the like acids.

Conversely said salt forms can be converted by treatment with an appropriate base into the free base form The term addition salt as used hereinabove also comprises the solvates which the compounds of formula (I) as well as the salts thereof, are able to form. Such solvates are for example hydrates, alcoholates and the like.

Quaternary amines of compounds of formula (I) as used herein defines which the compounds of formula (I) are able to form by reaction between a basic nitrogen of a compound of formula (I) and an appropriate quatenizing agent, such as, for example, an optionally substituted $C_{1-6}$alkylhalide, phenylmethylhalide, e.g. methyliodide or benzyliodide. Other reactants with good leaving groups may also be used, such as alkyl trifluoromethanesulfonates, alkyl methanesulfonates, and alkyl p-toluenesulfonates. A quaternary amine has a positively charged nitrogen. Pharmaceutically acceptable counterions include chloro, bromo, iodo, trifluoroacetate and acetate. The counterion of choice can be made using ion exchange resin columns.

The N-oxide forms of the compounds of formula (I), which may be prepared in art-known manners, are meant to comprise those compounds of formula (I) wherein a nitrogen atom is oxidized to the N-oxide.

The term "stereochemically isomeric forms" as used hereinbefore defines all the possible isomeric forms which the compounds of formula (I) may possess. Unless otherwise mentioned or indicated, the chemical designation of compounds denotes the mixture of all possible stereochemically isomeric forms, said mixtures containing all diastereomers and enantiomers of the basic molecular structure. More in particular, stereogenic centers may have the R- or S-configuration; substituents on bivalent cyclic (partially)

saturated radicals may have either the cis- or trans-configuration. Unless otherwise mentioned or indicated, the chemical designation of compounds denotes the mixture of all possible stereoisomeric forms, said mixtures containing all diastereomers and enantiomers of the basic molecular structure. The same applies to the intermediates as described herein, used to prepare end products of formula (I).

The terms cis and trans as used herein are in accordance with Chemical Abstracts nomenclature and refer to the position of the substituents on a ring moiety, more in particular on the homopiperidinyl ring in the compounds of formula (I).

The absolute stereochemical configuration of some compounds of formula (I) and of intermediates used in their preparation, was not experimentally determined. In those cases the stereochemically isomeric form which was first isolated is designated as "A" and the second as "B", without further reference to the actual stereochemical configuration. However, said "A" and "B" isomeric forms can be unambiguously characterized by for instance their optical rotation in case "A" and "B" have an enantiomeric relationship. A person skilled in the art is able to determine the absolute configuration of such compounds using art-known methods, e.g. X-ray diffraction.

A first group of compounds are those compounds of formula (I) wherein $R^1$ is hydrogen, $C_{1-6}$alkyl, aryl$^1$, $C_{1-6}$alkyl substituted with aryl$^1$, $C_{1-4}$alkyloxycarbonyl, aryl$^1$carbonyl, aryl$^1 C_{1-6}$alkylcarbonyl, $C_{1-4}$alkylcarbonyl, trifluoromethyl, trifluoromethylcarbonyl, $C_{1-6}$alkylsulfonyl, aryl$^1$sulfonyl, methanesulfonyl, benzenesulfonyl, trifluoromethanesulfonyl, or dimethylsulfamoyl;

$R^3$ is hydrogen, $C_{1-6}$alkyl, methanesulfonyl, benzenesulfonyl, trifluoromethanesulfonyl, dimethylsulfamoyl, $C_{1-4}$alkyl substituted with aryl$^2$ and optionally with hydroxy, $C_{1-4}$alkylcarbonylC$_{1-4}$alkyl substituted with aryl$^2$; and aryl$^1$ is phenyl; phenyl substituted with 1, 2 or 3 substituents each independently selected from halo, hydroxy, $C_{1-6}$alkyl, $C_{1-6}$alkyloxy, nitro, amino, cyano, or trifluoromethyl; pyridinyl; pyridinyl substituted with 1, 2 or 3 substituents each independently selected from halo, hydroxy, $C_{1-6}$alkyl, amino, diC$_{1-4}$alkylamino; naphthyl; quinolinyl; or 1,3-benzodioxolyl.

Interesting compounds are those compounds of formula (I) wherein X is NR$^3$, wherein R$^3$ is hydrogen, dimethylsulfamoyl, or $C_{1-4}$alkyl substituted with aryl$^2$.

Other interesting compounds are those compounds of formula (I) wherein the bivalent radical

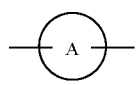

represents a radical of formula (a-1), (a-3) or (a-4) wherein R$^2$ represents hydrogen or hydroxy.

Particular compounds are those compounds of formula (I) wherein the bivalent radical -a$^1$=a$^2$-a$^3$=a$^4$- is of formula (b-1) wherein each hydrogen atom in said radicals (b-1) may optionally be replaced by halo, $C_{1-6}$alkyl, hydroxy, or $C_{1-6}$alkyloxy.

Other particular compounds are those compounds of formula (I) wherein the bivalent radical -a$^1$=a$^2$-a$^3$=a$^4$- is of formula (b-2) wherein each hydrogen atom in said radicals (b-2) may optionally be replaced by halo, $C_{1-6}$alkyl, hydroxy, or $C_{1-6}$alkyloxy.

Still other particular compounds are those compounds of formula (I) wherein the bivalent radical -a$^1$=a$^2$-a$^3$=a$^4$- is of formula (b-4) wherein each hydrogen atom in said radicals (b-4) may optionally be replaced by halo, $C_{1-6}$alkyl, hydroxy, or $C_{1-6}$alkyloxy.

Yet other particular compounds are those compounds of formula (I) wherein the bivalent radical -a$^1$=a$^2$-a$^3$=a$^4$- is of formula (b-5) wherein each hydrogen atom in said radicals (b-5) may optionally be replaced by halo, $C_{1-6}$alkyl, hydroxy, or $C_{1-6}$alkyloxy.

Preferred compounds of formula (I) are the compounds of formula (I) wherein the radical R$^1$ represents hydrogen, $C_{1-6}$alkyl, phenylmethyl, or furanylmethyl.

The compounds of the present invention can generally be prepared by reacting an intermediate of formula (II), or a functional derivative thereof such as a carboxylic acid, with an intermediate of formula (III) in the presence of polyphosphoric acid (PPA) or phosphorus oxychloride (POCl$_3$), at a temperature ranging between room temperature and the reflux temperature of the reaction mixture, optionally said reaction may be performed in a reaction-inert solvent.

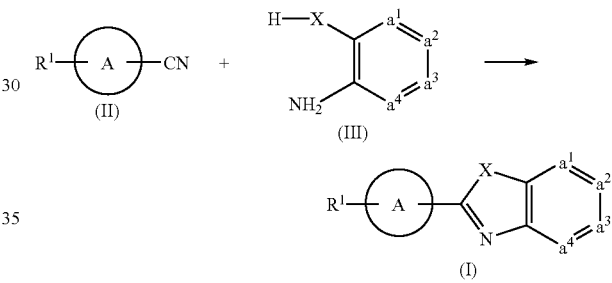

Compounds of formula (I-a), defined as compounds of formula (I) wherein R$^2$ represents hydroxy, can be prepared by reacting an intermediate of formula (IV) with an intermediate of formula (V). Said intermediate of formula (IV) is defined as a derivative of an intermediate of formula

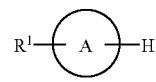

wherein two geminal hydrogen atoms are replaced by a carbonyl group.

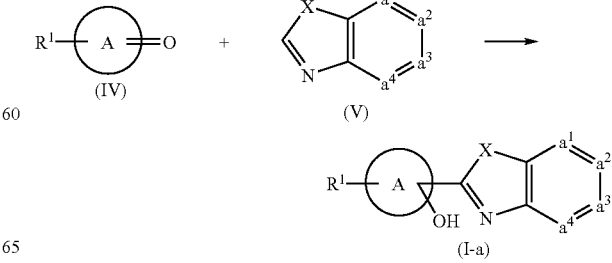

The compounds of formula (I) may also be converted into each other via art-known reactions or functional group transformations.

For instance, compounds of formula (I) wherein $R^1$ represents phenylmethyl can be converted into compounds of formula (I) wherein $R^1$ represents hydrogen by art-known debenzylation procedures. Said debenzylation can be performed following art-known procedures such as catalytic hydrogenation using appropriate catalysts, e.g. platinum on charcoal, palladium on charcoal, in appropriate solvents such as methanol, ethanol, 2-propanol, diethyl ether, tetrahydrofuran, and the like.

The compounds of formula (I) wherein $R^1$ is other than hydrogen, said $R^1$ being represented by $R^{1'}$ and said compounds by formula (I-c) can be prepared by N-alkylating a compound of formula (I) wherein $R^1$ is hydrogen, said compound being represented by (I-b), with an alkylating reagent of formula (VI).

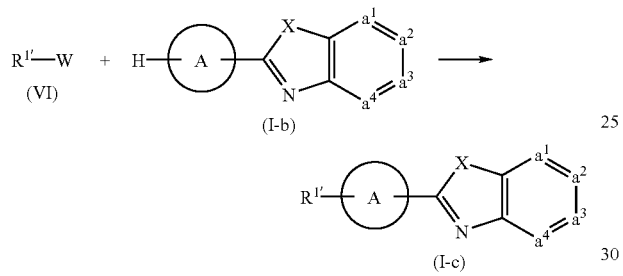

In formula (VI) and hereinafter W represents an appropriate leaving group such as, for example, halo, e.g. chloro, bromo and the like; or a sulfonyloxy group such as, for example, methanesulfonyloxy, 4-methylbenzenesulfonyloxy and the like. Said N-alkylation reaction can conveniently be conducted in a reaction-inert solvent such as, for example, an aromatic hydrocarbon, e.g., benzene, methylbenzene, dimethylbenzene and the like; an alkanol, e.g., methanol, ethanol, 1butanol and the like; a ketone, e.g., 2-propanone, 4-methyl-2-pentanone and the like; an ether, e.g., tetrahydrofuran, 1,4-dioxane, 1,1'-oxybisethane and the like; a dipolar aprotic solvent, e.g., N,N-dimethylformamide, N,N-dimethylacetamide, dimethyl sulfoxide, nitrobenzene, 1-methyl-2-pyrrolidinone and the like; or a mixture of such solvents. The addition of an appropriate base such as, for example, an alkali or an earth alkaline metal carbonate, hydrogen carbonate, alkoxide, hydride, amide, hydroxide or oxide, e.g., sodium carbonate, sodium hydrogen carbonate, potassium carbonate, sodium methoxide, sodium ethoxide, potassium tert. butoxide, sodium hydride, sodium amide, sodium hydroxide, calcium carbonate, calcium hydroxide, calcium oxide and the like; or an organic base, such as, for example, an amine, e.g., N,N-diethylethanamine, N-(1-methylethyl)-2-propanamine, 4-ethylmorpholine, pyridine and the like may be utilized to pick up the acid which is liberated during the course of the reaction. In some instances the addition of an iodide salt, preferably an alkali metal iodide, is appropriate. Somewhat elevated temperatures and stirring may enhance the rate of the reaction. Alternatively, said N-alkylation may be carried out by applying art-known conditions of phase transfer catalysis reactions.

Furthermore, compounds of formula (I) wherein $R^1$ is hydrogen, defined as compounds of formula (I-b), may be alkylated using art-known procedures such as, e.g. reductive N-alkylation with a suitable aldehyde or ketone, or compounds of formula (I) wherein $R^1$ is hydrogen can be reacted with an acyl halide or an acid anhydride.

Also, compounds of formula (I) wherein X is $NR^3$ and wherein $R^3$ represents methanesulfonyl, benzenesulfonyl, trifluoromethanesulfonyl, dimethylsulfamoyl can be converted into compounds of formula (I) wherein X is NH by art-known hydrolysis procedures, e.g. treatment with an aqueous acid such as HCl.

Those compounds of formula (I) wherein $R^2$ represent hydroxy can be converted into compounds of formula (I) wherein $R^2$ represents $C_{1-6}$alkyloxy using suitable alkylation conditions such as e.g. treatment with sodium hydride in tetrahydrofuran and addition of $C_{1-6}$alkyliodide.

Compounds of formula (I) wherein the bivalent radical

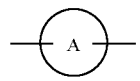

represents a radical of formula (a-1) or (a-7) wherein $R^2$ represents hydroxy, can be converted to compounds of formula (I) wherein the bivalent radical

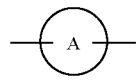

represents a radical of formula (a-3), (a-4), (a-8) or (a-9) wherein $R^2$ is hydrogen using art-known dehydratation procedures such as treatment with methanesulfonylchloride in a reaction-inert solvent such as $CH_2Cl_2$, or treatment with polyphosphoric acid (PPA), at a temperature ranging between room temperature and the reflux temperature of the reaction mixture, optionally said reaction may be performed in a reaction-inert solvent.

Conversely, compounds of formula (I) wherein the bivalent radical

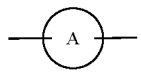

represents a radical of formula (a-2), (a-3), (a-4), (a-5), (a-6), (a-8) or (a-9) wherein $R^2$ is hydrogen, can be converted to compounds of formula (I) wherein the bivalent radical

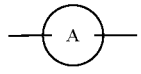

represents a radical of formula (a-1) or (a-7) wherein $R^2$ is hydrogen using art-known hydrogenation procedures such as treatment with hydrogen gas combination with a suitable catalyst such as, for example, palladium-on-charcoal, rhodium-on-carbon or platinum-on-charcoal.

The starting materials and some of the intermediates are known compounds and are commercially available or may be prepared according to conventional reaction procedures generally known in the art. For example, hexahydro-4H- azepine-4-one being an intermediates of formula (IV), 1H-benzimidazole and 1H-imidazo[4,5-b]-pyridine being intermediates of formula (V) are commercially available.

The compounds of formula (I) as prepared in the hereinabove described processes may be synthesized in the form of racemic mixtures of enantiomers which can be separated from one another following art-known resolution procedures. The racemic compounds of formula (I) may be converted into the corresponding diastereomeric salt forms by reaction with a suitable chiral acid. Said diastereomeric salt forms are subsequently separated, for example, by selective or fractional crystallization and the enantiomers are liberated therefrom by alkali. An alternative manner of separating the enantiomeric forms of the compounds of formula (I) involves liquid chromatography using a chiral stationary phase. Said pure stereochemically isomeric forms may also be derived from the corresponding pure stereochemically isomeric forms of the appropriate starting materials, provided that the reaction occurs stereospecifically. Preferably if a specific stereoisomer is desired, said compound will be synthesized by stereospecific methods of preparation. These methods will advantageously employ enantiomerically pure starting materials.

In view of the capability of the compounds of the present invention to relax the fundus, the subject compounds are useful to treat conditions related to a hampered or impaired relaxation of the fundus such as, e.g. gastro-oesophageal reflux, heartburn (including episodic heartburn, nocturnal heartburn, and meal-induced heartburn), dyspepsia, early satiety, bloating and anorexia.

Dyspepsia is described as a motility disorder. Symptoms can be caused by delayed gastric emptying, by impaired relaxation of the fundus to food ingestion or by hypersensitivity to gastric relaxation. Dyspeptic symptoms are for example a lack of appetite, feeling of fullness, early satiety, nausea, vomiting, bloating and gaseous eructation.

Warm-blooded animals, including humans, (generally called herein patients) suffering from dyspeptic symptoms as a result of delayed gastric emptying usually have a normal fundic relaxation and can be relieved of their dyspeptic symptoms by administering a prokinetic agent such as, e.g. cisapride.

Patients can have dyspeptic symptoms without having a disturbed gastric emptying. Their dyspeptic symptoms may result from a hypercontracted fundus resulting in a diminished compliance and abnormalities in the adaptive fundic relaxation. Also dyspeptic symptoms may arise from hypersensitivity of the fundus to relaxation.

A hypercontracted fundus results in a diminished compliance of the stomach The "compliance of the stomach" can be expressed as the ratio of the volume of the stomach over the pressure exerted by the stomach wall. The compliance of the stomach relates to the gastric tone, which is the result of the tonic contraction of muscle fibers of the proximal stomach. This proximal part of the stomach, by exerting a regulated tonic contraction (gastric tone), accomplishes the reservoir function of the stomach.

Patients suffering from early satiety cannot finish a normal meal since they feel saturated before they are able to finish said normal meal. Normally when a subject starts eating, the stomach will show an adaptive relaxation, i.e. the stomach will relax to accept the food that is ingested. This adaptive relaxation is not possible when the compliance of the stomach is hampered which results in an impaired relaxation of the fundus.

In view of the utility of the compounds of formula (I), it follows that the present invention also provides a method of treating warm-blooded animals, including humans, (generally called herein patients) suffering from impaired relaxation of the fundus to food ingestion. Consequently a method of treatment is provided for relieving patients suffering from conditions, such as, for example, gastro-oesophageal reflux, heartburn (including episodic heartburn, nocturnal heartburn, and meal-induced heartburn), dyspepsia, early satiety, bloating and anorexia.

Hence, the use of a compound of formula (I) as medicine is provided, and in particular the use of a compound of formula (I) for the manufacture of a medicine for treating conditions involving an impaired relaxation of the fundus to food ingestion. Both prophylactic and therapeutic treatment are envisaged.

The symptoms of impaired fundic relaxation may also arise due to the intake of chemical substances, e.g. Selective Seretonine Re-uptake Inhibitors (SSRI's), such as fluoxetine, paroxetine, fluvoxamine, citalopram, sertraline; or erythromycin and erythromycin alike antibiotic macrolides such as, e.g. EM-523, EM-574, ABT-229, GM-611, (8R)-4"-deoxy-6,9-epoxyerythromycin A, (8S)-4"-deoxy-6,9-epoxyerythromycin A, A-81648, A-173508, A-182061, and KC-11458.

Another functional gastrointestinal disorder is irritable bowel syndrome whereby one of its features is believed to be related to hypersensitivity of the gut to distension. Hence it is therefore believed that modulation of said hypersensitivity by the compounds of the present invention having fundus relaxation properties may result in a reduction of the symptoms in subjects suffering from IBS. Accordingly the use of a compound of formula (I) for the manufacture of a medicine for treating IBS (irritable bowel syndrome) is provided. Furthermore the compounds of formula (I) are also able to reduce the pain associated with gastrointestinal hypersensitivity.

To prepare the pharmaceutical compositions of this invention, an effective amount of the particular compound, in base or acid addition salt form, as the active ingredient is combined in intimate admixture with a pharmaceutically acceptable carrier, which carrier may take a wide variety of forms depending on the form of preparation desired for administration. These pharmaceutical compositions are desirably in unitary dosage form suitable, preferably, for administration orally, rectally or by parenteral injection. For example, in preparing the compositions in oral dosage form, any of the usual pharmaceutical media may be employed, such as, for example, water, glycols, oils, alcohols and the like in the case of oral liquid preparations such as suspensions, syrups, elixirs and solutions; or solid carriers such as starches, sugars, kaolin, lubricants, binders, disintegrating agents and the like in the case of powders, pills, capsules and tablets. Because of their ease in administration, tablets and capsules represent the most advantageous oral dosage unit form, in which case solid pharmaceutical carriers are obviously employed. For parenteral compositions, the carrier will usually comprise sterile water, at least in large part, though other ingredients, for example, to aid solubility, may be included. Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed. In the compositions suitable for percutaneous administration, the carrier optionally comprises a penetration enhancing agent and/or a suitable wetting agent, optionally combined with suitable additives of any nature in minor proportions, which additives do not cause a significant deleterious effect to the skin. Said additives may facilitate the administration to the skin and/or may be helpful for preparing the desired compositions. These compositions may be administered in various ways, e.g., as a transdermal patch, as a spot-on, as an ointment. Acid addition salts of (I) due to their increased water solubility over the corresponding base form, are obviously more suitable in the preparation of aqueous compositions.

It is especially advantageous to formulate the aforementioned pharmaceutical compositions in dosage unit form for ease of administration and uniformity of dosage. Dosage unit form as used in the specification and claims herein refers to physically discrete units suitable as unitary dosages, each unit containing a predetermined quantity of active ingredient calculated to produce the desired therapeutic effect in association with the required pharmaceutical carrier. Examples of such dosage unit forms are tablets (including scored or coated tablets), capsules, pills, powder packets, wafers, injectable solutions or suspensions, teaspoonfuls, tablespoonfuls and the like, and segregated multiples thereof.

For oral administration, the pharmaceutical compositions may take the form of solid dose forms, for example, tablets (both swallowable-only and chewable forms), capsules or gelcaps, prepared by conventional means with pharmaceutically acceptable excipients such as binding agents (e.g. pregelatinised maize starch, polyvinylpyrrolidone or hydroxypropyl methylcellulose); fillers (e.g. lactose, microcrystalline cellulose or calcium phosphate); lubricants e.g. magnesium stearate, talc or silica); disintegrants (e.g. potato starch or sodium starch glycollate); or wetting agents (e.g. sodium lauryl sulphate). The tablets may be coated by methods well known in the art.

Liquid preparations for oral administration may take the form of, for example, solutions, syrups or suspensions, or they may be presented as a dry product for constitution with water or other suitable vehicle before use. Such liquid preparations may be prepared by conventional means, optionally with pharmaceutically acceptable additives such as suspending agents (e.g. sorbitol syrup, methylcellulose, hydroxy-propyl methylcellulose or hydrogenated edible fats); emulsifying agents (e.g. lecithin or acacia); non-aqueous vehicles (e.g. almond oil, oily esters or ethyl alcohol); and preservatives (e.g. methyl or propyl p-hydroxybenzoates or sorbic acid).

Pharmaceutically acceptable sweeteners comprise preferably at least one intense sweetener such as saccharin, sodium or calcium saccharin, aspartame, acesulfame potassium, sodium cyclamate, alitame, a dihydrochalcone sweetener, monellin, stevioside or sucralose (4,1',6'-trichloro-4,1',6'-trideoxygalactosucrose), preferably saccharin, sodium or calcium saccharin, and optionally a bulk sweetener such as sorbitol, mannitol, fructose, sucrose, maltose, isomalt, glucose, hydrogenated glucose syrup, xylitol, caramel or honey.

Intense sweeteners are conveniently employed in low concentrations. For example, in the case of sodium saccharin, the concentration may range from 0.04% to 0.1% (w/v) based on the total volume of the final formulation, and preferably is about 0.06% in the low-dosage formulations and about 0.08% in the high-dosage ones. The bulk sweetener can effectively be used in larger quantities ranging from about 10% to about 35%, preferably from about 10% to 15% (w/v).

The pharmaceutically acceptable flavours which can mask the bitter tasting ingredients in the low-dosage formulations are preferably fruit flavours such as cherry, raspberry, black currant or strawberry flavour. A combination of two flavours may yield very good results. In the high-dosage formulations stronger flavours may be required such as Caramel Chocolate flavour, Mint Cool flavour, Fantasy flavour and the like pharmaceutically acceptable strong flavours. Each flavour may be present in the final composition in a concentration ranging from 0.05% to 1% (w/v). Combinations of said strong flavours are advantageously used. Preferably a flavour is used that does not undergo any change or loss of taste and colour under the acidic conditions of the formulation.

The compounds of the invention may be formulated for parenteral administration by injection, conveniently intravenous, intramuscular or subcutaneous injection, for example by bolus injection or continuous intravenous infusion. Formulations for injection may be presented in unit dosage form e.g. in ampoules or in multidose containers, with an added preservative. The compositions may take such forms as suspensions, solutions or emulsions in oily or aqueous vehicles, and may contain formulatory agents such as isotonizing, suspending, stabilising and/or dispersing agents. Alternatively, the active ingredient may be in powder form for constitution with a suitable vehicle, e.g. sterile pyrogen-free water before use.

The compounds of the invention may also be formulated in rectal compositions such as suppositories or retention enemas, e.g. containing conventional suppository bases such as cocoa butter or other glycerides.

Those of skill in the treatment of conditions related to a hampered or impaired relaxation of the fundus could easily determine the effective daily amount from the test results presented hereinafter. In general it is contemplated that a therapeutically effective dose would be from 0.001 mg/kg to 5 mg/kg body weight, more preferably from 0.01 mg/kg to 0.5 mg/kg body weight. It may be appropriate to administer the therapeutically effective dose as two, three, four or more sub-doses at appropriate intervals throughout the day. Said sub-doses may be formulated as unit dosage forms, for example, containing 0.1 mg to 350 mg, and in particular 1 to 200 mg of active ingredient per unit dosage form.

The exact dosage and frequency of administration depends on the particular compound of formula (I) used, the particular condition being treated, the severity of the condition being treated, the age, weight and general physical condition of the particular patient as well as other medication the patient may be taking, as is well known to those skilled in the art. Furthermore, it is evident that said effective daily amount may be lowered or increased depending on the response of the treated patient and/or depending on the evaluation of the physician prescribing the compounds of the instant invention. The effective daily amount ranges mentioned hereinabove are therefore only guidelines.

EXPERIMENTAL PART

In the procedures described hereinafter the following abbreviations were used: "ACN" stands for acetonitrile; "THF", which stands for tetrahydrofuran; "DCM" stands for dichloromethane; "DIPE" stands for diisopropylether; and "DMF" means N,N-dimethyl-formamide.

For some chemicals the chemical formula was used, e.g. $H_2$ for hydrogen gas, $N_2$ for nitrogen gas, $CH_2Cl_2$ for dichloromethane, $CH_3OH$ for methanol, $NH_3$ for ammonia, HCl for hydrochloric acid, and NaOH for sodium hydroxide.

In those cases the stereochemically isomeric form which was first isolated is designated as "A" and the second as "B", without further reference to the actual stereochemical configuration.

A. PREPARATION OF THE INTERMEDIATES

Example A.1

A mixture of hexahydro-1-(phenylmethyl)-4H-azepin-4-one (0.2 mol) and 4-toluene-sulfonylmethyl isocyanide (0.25 mol) in DMF (200 ml) was stirred at 0° C. A solution of potassium tert-butoxide (0.4 mol) in a mixture of 2-methyl-2-propanol (200 ml) and 1,2-dimethoxyethane (200 ml) was added dropwise at 0° C. The mixture was allowed to reach room temperature and stirring was continued for 1 hour. The mixture was stirred in water and this mixture was extracted with DCM. The separated organic layer was dried, filtered and the solvent was evaporated, yielding 48 g of (±)-hexahydro-1-(phenylmethyl)-1H-azepine-4-carbonitrile (intermediate 1).

Example A.2

Dimethyl sulfamoyl chloride (0.39 mol) was added to a mixture of 1H-imidazo[4,5-b]-pyridine (0.26 mol) and triethylamine (0.65 mol) in toluene (500 ml). The mixture was stirred at 100° C. for 24 hours. The solvent was evaporated. The residue was taken up in DCM. The organic solution was washed with water and with $K_2CO_3$ (10%), dried, filtered and the solvent evaporated, yielding 45.4 g (77%) of a mixture of N,N-dimethyl-1H-imidazo[4,5-b]pyridine-1-sulfonamide (intermediate 2) and N,N-dimethyl-3H-imidazo[4,5-b]pyridine-3-sulfonamide (intermediate 3).

Example A.3 a) A mixture of ethyl hexahydro-4-oxoazepine-1-carboxylate (0.585 mol), 1,2-ethane-diol (0.585 mol) and p-toluene-sulfonic acid (0.0058 mol) in toluene (800 ml) was stirred and refluxed overnight, using a water separator (10.5 ml was separated). The solvent was evaporated, yielding 142.5 g of ethyl 1,4-dioxa-8-azaspiro[4.6]undecane-8-carboxylate (intermediate 4).

b) A mixture of intermediate (4) (0.585 mol) and KOH (5.85 mol) in 2-propanol (1200 ml) was stirred and refluxed overnight. The solvent was evaporated. The residue was stirred in water and this mixture was extracted with DCM. The separated organic layer was dried, filtered, and the solvent evaporated, yielding 57.7 g of 1,4-dioxa-8-azaspiro[4.6]undecane (intermediate 5).

c) A mixture of intermediate (5) (0.114 mol), 1-(2-bromoethyl)-4-methoxy-benzene (0.172 mol) and $K_2CO_3$ (0.219 mol) in ACN (200 ml) was stirred at 80° C. for 2 hours. Water was added and the mixture was extracted with DCM. The organic layer was separated, dried, filtered and the solvent was evaporated. The residue was purified by column chromatography over silica gel (eluent: $CH_2Cl_2$/$CH_3OH$/$NH_4OH$ 95/5/0.2). The pure fractions were collected and the solvent was evaporated, yielding 28.5 g of 8-[2-(4-methoxyphenyl)ethyl]-1,4-dioxa-8-azaspiro[4.6]undecane (intermediate 6).

d) A mixture of intermediate (6) (0.098 mol) in HCl (3 N, 300 ml) and THF (300 ml) was stirred at 60° C. for 1 hour. The mixture was basified with solid $K_2CO_3$ and extracted with ethyl acetate. The organic layer was separated, dried, filtered and the solvent was evaporated, yielding 22.6 g of hexahydro-1-[2-(4-methoxyphenyl)ethyl]-4H-azepin-4-one (intermediate 7).

Example A.4 a) 5,6,7,8-Tetrahydro-2(1H)-quinolinone (0.134 mol) was added portionwise at 5° C. to sulfuric acid (200 ml). Then $HNO_3$ (0.235 mol) was added portionwise while the temperature was kept below 10° C. The mixture was stirred at 5° C. for 1 hour, poured out carefully into a small amount of ice water and stirred at 0° C. for 10 min. The precipitate was filtered off and dried, yielding 14.2 g (55%) of 5,6,7,8-tetrahydro-3-nitro-2(1H)-quinolinone (intermediate 8)

b) A solution of intermediate (8) (0.072 mol) and BTEAC (0.0362 mol) in ACN (150 ml) was stirred at room temperature. Phosphoric trichloride (0.222 mol) was added dropwise. The mixture was stirred and refluxed for 8 hours. The solvent was evaporated till dryness. The residue was poured out into water and $NH_4OH$. The mixture was extracted with DCM. The organic layer was separated, dried, filtered and the solvent was evaporated, yielding 15 g of 2-chloro-5,6,7,8-tetrahydro-3-nitroquinoline (intermediate 9).

c) A mixture of intermediate (9) (0.0658 mol) in $NH_3$/$CH_3OH$ 7N (60 ml) was stirred at 120° C. for 12 hours in an autoclave. The solvent was evaporated till dryness. The residue was taken up in 2-propanone. The precipitate was filtered off and dried, yielding 8.6 g 5,6,7,8-tetrahydro-3-nitro-2-quinolinamine (intermediate 10). d) A mixture of intermediate (10) (0.031 mol) in methanol (100 ml) was hydrogenated at room temperature under a $3.10^5$ Pa (3 bar) pressure for 30 minutes in a Parr apparatus. After uptake of hydrogen (3 equivalents), the catalyst was filtered through celite, rinced with methanol and the filtrate was evaporated till dryness. The product was used with further purification, yielding 5.07 g 5,6,7,8-tetrahydro-2,3-quinolinediamine (intermediate 11).

B. PREPARATION OF THE FINAL COMPOUNDS

Example B.1

Polyphosphoric acid (PPA) (10 g) was heated to 160° C. Intermediate (1) (0.0467 mol) and 2,3-diaminopyridine (0.0513 mol) were added. The mixture was stirred at 180° C. for 1 hour, poured out on $K_2CO_3$ solid and ice, washed with $K_2CO_3$ 10% and extracted with DCM. The aqueous layer was washed with DCM. The organic layer was dried, filtered and the solvent was evaporated. This fraction was purified by column chromatography over silica gel (eluent: $CH_2Cl_2$/$CH_3OH$/$NH_4OH$ 94/6/0.5). The pure fractions were collected and the solvent was evaporated. Part of this fraction (6 g) was crystallized from DIPE and 2-propanone. The precipitate was filtered off and dried, yielding 3.16 g of (±)-2-[hexahydro-1-(phenylmethyl)-1H-azepin-4-yl]-1H-imidazo[4,5-b]pyridine (compound 69).

In analogy, compound (207) was prepared by reacting intermediate (1) with 2-amino-benzenethiol.

Example B.2

Compound (69) (0.0653 mol) was separated into its enantiomers by chiral column chromatography (eluent: hexane/ethanol/$Et_3N$ 95/5/0.1; column: CHIRALPAK AD 20 µm). The resolved fractions were collected and their solvents were evaporated, and crystallized from DIPE or 2-propanone, yielding 4.64 g (23%) of (−)-2-[hexahydro-1-(phenylmethyl)-1H-azepin-4-yl]-1H-imidazo[4,5-b]pyridine (compound 80) $[\alpha]_D^{20}$=−15.08° (c=8.49 mg/ml in $CH_3OH$); and 6.19 g (31%) of (+)-2-[hexahydro-1-(phenylmethyl)-1H-azepin-4-yl]-1H-imidazo[4,5-b]pyridine (compound 81), $[\alpha]_D^{20}$=+15.52° (c=8.70 mg/5 ml in $CH_3OH$).

Example B.3 n-Butyllithium (1.6M in hexanes, 0.164 mol) was added dropwise at −30° C. under N₂ flow to a mixture of N-(1-methylethyl)-2-propanamine (0.164 mol) in THF (70 ml). The mixture was cooled to −70° C. A mixture of 1-methyl-1H-imidazo[4,5-b]pyridine (0.0751 mol) in THF (70 ml) was added dropwise. The mixture was stirred for 1 hour. A mixture of hexahydro-1-(phenylmethyl)-4H-azepin-4-one (0.0787 mol) in THF (60 ml) was added at −70° C. The mixture was stirred at −70° C. for 2 hours, brought to 0° C., poured out into water and NH₄Cl and extracted with DCM and a small amount of methanol. The organic layer was separated, dried, filtered and evaporated to dryness. The residue was purified by column chromatography over silica gel (eluent: CH₂Cl₂/CH₃OH/NH₄OH 97/3/0.5). The desired fractions were collected and the solvent was evaporated, yielding 8.8 g of (±)-hexahydro-4-(1-methyl-1H-imidazo[4,5-b]pyridin-2-yl)-1-(phenylmethyl)-1H-azepin-4-ol (compound 152).

Example B.4

A mixture of compound (81) (0.0068 mol) in methanol (20 ml) was hydrogenated at 40° C. under a 3.10⁵ Pa (3 bar) pressure with palladium-on-carbon (1 g) as a catalyst. After uptake of hydrogen (1 equivalent), the catalyst was filtered over celite and the filtrate was evaporated. The residue was crystallized from ACN. The precipitate was filtered off and dried, yielding 0.95 g of (A)-2-(hexahydro-1H-azipin-4-yl)-1H-imidazo[4,5-b]pyridine (compound 102).

Example B.5

K₂CO₃ (0.011 mol) and then 1-(chloromethyl)-4-methoxybenzene (0.011 mol) were added to a mixture of compound (87) (0.011 mol) in ACN (80 ml). The mixture was stirred at room temperature overnight. The solvent was evaporated till dryness. The residue was taken up in DCM and water. The organic layer was separated, dried filtered and the solvent was evaporated. The residue was purified by column chromatography over silica gel (eluent: CH₂Cl₂/CH₃OH/NH₄OH 93/7/0.5). The pure fractions were collected and the solvent was evaporated. The residue was crystallized from ACN. The precipitate was filtered off, dried, yielding 1.2 g of (±)-2-[hexahydro-1-[(4-methoxyphenyl)methyl]-1H-azepin-4-yl]-1H-imidazo[4,5-b]pyridine (compound 101).

Example B.6

Polyphosphoric acid (PPA) (10 g) was heated to 160° C. Compound (155) (0.0043 mol) was added. The mixture was stirred for 20 minutes, cooled, poured out into ice water, saturated with K₂CO₃ (powder), and extracted with CH₂Cl₂/CH₃OH (95/5). The organic layer was separated, dried, filtered and the solvent was evaporated till dryness. The residue was taken up in CH₃OH/CH₃CN. The precipitate was filtered off, rinced and dried, yielding 1.55 g (20.9%) of 2-(2,3,6,7-tetrahydro-1H-azepin-4-yl)-1H-imidazo[4,5-b]pyridine (compound 116). The mother layer was evaporated till dryness, yielding 5.5 g of a mixture of compound (116) and 2-(2,5,6,7-tetrahydro-1H-azepin-4-yl)-1H-imidazo[4,5-b]pyridine (compound 115).

Example B.7

A mixture of compound (136) (0.0276 mol) in DCM (80 ml) was cooled to 5° C. 3-Chlorobenzenecarboperoxoic acid (0.044 mol) was added. The mixture was kept at 5° C. for 1 hour, then brought to room temperature overnight. K₂CO₃ 10% was added. The mixture was saturated with K₂CO₃ (powder) and extracted with CH₂Cl₂/CH₃OH. The organic layer was separated, dried, filtered and the solvent was evaporated till dryness. The residue was purified by column chromatography over silica gel (eluent: CH₂Cl₂/CH₃OH/NH₄OH 92/8/0.5). The pure fractions were collected and the solvent was evaporated, yielding 6.5 g (74.7%) of (±)-1-(2,2-dimethyl-1-oxopropyl)-4-(1H-imidazo[4,5-b]pyridin-2-yl)-1H-azepine, N4-oxide (compound 161).

Example B.8

3-Chlorobenzenecarboperoxoic acid (0.0157 mol) was added portionwise at room temperature to a mixture of compound (69) (0.013 mol) in DCM (80 ml). The mixture was stirred at room temperature for 4 hours. A saturated NaHCO₃ solution was added. The mixture was extracted with DCM, saturated with K₂CO₃ and extracted again with CH₂Cl₂/2-propanol. The organic layer was separated, dried, filtered and the solvent was evaporated at a temperature below 40° C. The residue was purified by column chromatography over silica gel (eluent: CH₂Cl₂/CH₃OH/NH₄OH 88/12/1). Two pure fractions were collected and their solvents were evaporated, yielding 2.3 g of (A)-2-[hexahydro-1-(phenylmethyl)-1H-azepin-4-yl]-1H-imidazo[4,5-b]pyridine, N-oxide (compound 113) and 1.6 g of (B)-2-[hexahydro-1(phenylmethyl)-1H-azepin-4-yl]-1H imidazo[4,5-b]pyridine, N-oxide (compound 114).

Example B.9

NaH 80% (0.0195 mol) was added portionwise at 5° C. to a mixture of compound (±)-2-[hexahydro-1-(phenylmethyl)-1H-azepin-4-yl]-1H-imidazo[4,5-b]pyridine (0.0195 mol) in DMF (100 ml). The mixture was stirred for 15 minutes. 2-Bromo-1-phenylethanone (0.0214 mol) was added. The mixture was stirred for 30 minutes. Water was added and the mixture was extracted with ethyl acetate. The organic layer was separated, dried, filtered and the solvent was evaporated. The residue was purified by column chromatography over silica gel (eluent: CH₂Cl₂/CH₃OH/NH₄OH 97/3/0.1). Three pure fractions were collected, their solvents were evaporated, converted into the hydrochloric acid salt (1:2) with HCl/2-propanol, and crystallized from 2-propanol, yielding 3.3 g (±)-2-[2-[hexahydro-1-(phenylmethyl)-1H-azepin-4-yl]-3H-imidazo[4,5-b]pyridin-3-yl]-1-phenylethanone hydrochloride (1:2) (compound 76).

Example B.10

A solution of compound (143) (0.00838 mol) in HCl 3N (35 ml) and THF (35 ml) was stirred at room temperature overnight, neutralized with K₂CO₃ solid and extracted with ethyl acetate. The organic layer was separated, dried filtered and the solvent was evaporated. The residue was purified by column chromatography over silica gel (eluent: CH₂Cl₂/CH₃OH/NH₄OH 90/10/0.5). The pure fractions were collected and the solvent was evaporated. The residue was crystallized from 2-propanone. The precipitate was filtered off and dried, yielding 1.54 g of (±)-hexahydro-4-(1H-imidazo[4,5-b]pyridin-2-yl)-1-(phenylmethyl)-1H-azepin-4-ol (compound 149).

Example B.11

A mixture of compound (54) and compound (55) in methanol (50 ml) was hydrogenated at 40° C. under a $5.10^5$ Pa (5 bar) pressure for 8 hours with palladum-on-carbon (0.45 g) as a catalyst. After uptake of hydrogen (1 equivalent), the catalyst was filtered through celite, washed with methanol and the filtrate was evaporated. The residue was purified by column chromatography over silica gel (eluent : $CH_2Cl_2/CH_3OH/NH_4OH$ 90/10/1). The pure fractions were collected and the solvent was evaporated. The residue was crystallized from diethyl ether. The precipitate was filtered off and dried, yielding 1.8 g of compound (14).

Example B.12

A mixture of compound (27) (0.0059 mol) in methanol (100 ml) was stirred at 5° C. Sodium borohydride (0.0059 mol) was added portionwise under $N_2$ flow. The mixture was stirred at room temperature for 2 hours and hydrolized with water. Methanol was evaporated. The residue was taken up in DCM and the mixture was extracted. The organic layer was separated, dried, filtered and the solvent was evaporated. The residue was converted into the ethanedioic acid salt (1:2). The mixture was crystallized from 2-propanone. The precipitate was filtered off and dried, yielding 2.37 g of compound (29).

Example B.13

A mixture of compound (31) (0.00659 mol) and methyl iodide (0.00923 mol) in 2-propanone (80 ml) was stirred at room temperature for 12 hours. The precipitate was filtered off, washed with 2-propanone and dried, yielding 2.45 g of compound (154).

Example B.14

A mixture of compound (161) in HCl 12N (50 ml) was stirred and refluxed overnight. The solvent was evaporated till dryness. The residue was taken up in $K_2CO_3$ 10% and saturated with $K_2CO_3$ powder. The mixture was extracted with $CH_2Cl_2/CH_3OH$ 90/10. The organic layer was separated, dried, filtered and the solvent was evaporated till dryness. The residue was crystallized from $CH_3OH/CH_3CN/$ DIPE. The precipitate was filtered off and dried, yielding 1.2 g compound (162).

Example B.15

A mixture of compound (126) (0.00594 mol) in HBr 48% in water (60 ml) was stirred at 90° C. for 12 hours. The solvent was evaporated. The residue. was washed with a solution of $K_2CO_3$ and extracted with ethyl acetate and DCM. The organic layer was separated, dried, filtered and the solvent was evaporated. The residue was taken up in ethyl acetate. The mixture was allowed to crystallize out. The precipitate was filtered off and dried, yielding 0.8 g of compound (127).

Example B.16

A mixture of compound (92) (0.006 mol) in methanol (20 ml) was hydrogenated at room temperature under a $3.10^5$ Pa (3 bar) pressure for 2 hours with Raney nickel (2 g) as a catalyst. After uptake of hydrogen (3 equivalents), the catalyst was filtered through celite and the filtrate was evaporated, yielding 2.1 g of compound (105).

Example B.17

A mixture of compound (87) (0.0139 mol) in triethylamine (2.9 ml) and DCM (30 ml) was stirred at room temperature for 15 minutes. 3-Pyridinecarboxylic acid (0.0209 mol) was added. A mixture of 1-hydroxy-1H-benzotriazole (0.0209 mol) in DCM (30 ml) was added at 5° C. under $N_2$ flow. A mixture of N,N'-methanetetrayl-biscyclohexanamine (0.0209 mol) in DCM (30 ml) was added dropwise. The mixture was stirred at room temperature for 6 hours. The precipitate was filtered off. The filtrate was washed with water. The organic layer was separated, dried, filtered and the solvent was evaporated. The residue was purified by column chromatography over silica gel (eluent: $CH_2Cl_2/CH_3OH/NH_{40}H$ 92/8/0.5). Two fractions were collected and their solvents were evaporated. Both fractions were combined and crystallized from DCM and DIPE, yielding 2.3 g of compound (118).

Example B.18

Triethylamine (0.0111 mol) was added to a mixture of compounds (115) and (116), as prepared in Example B.6, in DMF (40 ml). The mixture was cooled on an ice-bath. Methanesulfonyl chloride (0.01 mol) was added. The mixture was stirred at 5° C. for 1 hour and then stirred at room temperature overnight. The solvent was evaporated till dryness. The residue was taken up in a mixture of DCM and water. The organic layer was separated, dried, filtered and the solvent was evaporated till dryness. The residue was purified by column chromatography (eluent: $CH_2Cl_2/$ $CH_3OH/NH_4OH$ 95/5/0.1) over silica gel, and crystallized from 2-propanone and DIPE. The precipitate was filtered off and dried, yielding 1.25 g of compound (180) (mp.>260° C.).

Example B.19

Triethylamine (0.0168 mol) was added to a mixture of compounds (115) (0.007 mol) and (116) (0.007 mol), as prepared in Example B.6, in DMF (60 ml). The mixture was cooled at 5° C. and 2-phenylacetyl chloride (0.0154 mol) was added. The mixture was stirred at 5° C. for 1 hour, then at room temperature overnight, evaporated till dryness and taken up in a mixture of DCM and water. The organic layer was separated, dried, filtered and the solvent was evaporated till dryness. The residue was purified by column chromatography over silica gel (eluent: $CH_2Cl_2/CH_3OH/NH_4OH$ 95/5/0.2). Two fractions were collected and the solvent was evaporated. One fraction was crystallized from $CH_3CN/$ DIPE. The precipitate was filtered off and dried, yielding 0.25 g of compound (182) (mp. 169° C.). The second fraction was crystallized from $CH_3CN/DIPE$. The precipitate was filtered off and dried, yielding: 1.55 g of compound (183) (mp. 157° C.).

Example B.20

Triethylamine (0.037 mol) then ethyl chloroformate (0.074 mol) were added dropwise at room temperature to a mixture of compound (87) (0.0185 mol) in toluene (60 ml). The mixture was stirred at 95° C. for 2 hours, poured out into ice water and extracted with ethyl acetate. The organic layer was separated, dried, filtered and the solvent was evaporated. The residue was purified by column chromatography over silica gel (eluent: $CH_2Cl_2/CH_3OH/NH_4OH$ 97/3/0.5). One fraction was collected and the solvent was evaporated, yielding 3.7 g of compound (187).

Example B.21

A mixture of compound (187) (0.0083 mol) and potassium hydroxide (0.053 mol) in 2-propanol (30 ml) was stirred and refluxed overnight, poured out into ice water, extracted with DCM and washed with water. The organic layer was separated, dried, filtered and the solvent was evaporated till dryness. The mixture was taken up in diethyl ether/DIPE. The precipitate was filtered, washed and dried, yielding 1.45 g of compound (188) (mp. 141° C.).

Example B.22

A mixture of methyl 5,6-diaminonicotinate (0.0104 mol) and hexahydro-1-(phenylmethyl)-1H-azepine-4-carboxylic acid (0.0087 mol) in phosphoroxychloride (50 ml) was stirred at 110° C. for 8 hours. The solvent was evaporated. The residue was basified with $K_2CO_3/H_2O$. The mixture was satured with $K_2CO_3$ and extracted with a mixture of ethyl acetate and isopropanol. The organic layer was separated, dried, filtered, and the solvent was evaporated. The residue was purified by column chromatography over silica gel (eluent: $CH_2Cl_2/CH_3OH/NH_4OH$; 95/5/0.5) and crystallized from $CH_3CN$/DIPE, yielding 1.02 g of compound (217) (mp. 150° C.).

Example B.23 a) A mixture of 3-amino-2-pyridinol (0.018 mol) in DCM (40 ml) was cooled to 5° C. Triethylamine (0.0216 mol) was added. A mixture of hexahydro-1-(phenylmethyl)-1H-azepine-4-carbonyl chloride (0.018 mol) in ACN (40 ml) was added. The mixture was stirred at 5° C. for 1 hour, then stirred at room temperature overnight and poured out into water. The organic layer was separated. dried, filtered and the solvent was evaporated till dryness. The residue was used without further purification, yielding intermediate (12).

b) A mixture of intermediate (12) (0.018 mol) in phosphoroxychloride (80 ml) was stirred and refluxed overnight. Phosphoroxychloride was evaporated till dryness. The residue was taken up in $K_2CO_3$ 10% and extracted with DCM. The organic layer was separated, dried, filtered, and the solvent was evaporated till dryness. The residue was purified by column chromatography over silica gel (eluent: $CH_2Cl_2/CH_3OH/NH_4OH$; 90/10/0.1), crystallized from ACN and converted into the ethanedioic acid salt, yielding 0.8 g of compound (213) (mp. 102° C.).

Example B.24

A mixture of N-(2-amino-3-pyridinyl)hexahydro-1-(phenylmethyl)-1H-azepine-3-carboxamide (0.0151 mol) and APTS (0.1 g) in xylene (150 ml) was stirred and refluxed for 12 hours, evaporated and taken up in $K_2CO_3$ 10%/$CH_2Cl_2$. The organic layer was separated, dried, filtered and the solvent was evaporated. The residuewas purified by column chromatography over silica gel (eluent: $CH_2Cl_2/CH_3OH/NH_4OH$ 96/4/0.5 to 90/10/0.5). The pure fractions were collected and crystallized from $CH_3CN$/DIPE, yielding 2.57 g of compound (195) (nip. 139° C.).

Example B.25

A mixture of N-(2-chloro-3-pyridinyl)hexahydro-1-(phenylmethyl)-1H-azepine-4-carboxamide (0.096 mol), Lawesson's reagent (0.0096 mol) in HMPT (33 ml) was stirred at 150° C. overnight. The mixture was poured out into $K_2CO_3$/ice and extracted with ethyl acetate. The organic layer was separated, dried, filtered, and the solvent was evaporated. The residue was purified by column chromatography over silica gel (eluent: $CH_2Cl_2/CH_3OH/NH_4OH$; 97.5/2.5/0.1). The pure fractions were collected and the solvent was evaporated. The residue was dissolved in 2-propanone and converted into the ethanedioic acid salt. The precipitate was filtered off and dried., yielding 0.52 g of compound (218) (mp. 163° C.).

Example B.26

A mixture of 1-chloroethyl chloroformate (0.0188 mol) in 1,2-dichloroethane (20 ml) was added dropwise at 0° C. to a mixture of compound (206) (0.0172 mol) in 1,2-dichloroethane (100 ml). The mixture was brought to room temperature then stirred at 80° C. for 1 hour. The solvent was evaporated till dryness. Methanol (60 ml) was added. The mixture was kept at room temperature for 12 hours then stirred and refluxed for 30 minutes. The solvent was evaporated. $K_2CO_3$ (10%)/$CH_2Cl_2$ was added The organic layer was separated, dried, filtered, and the solvent was evaporated. The residue was crystallized from ACN, yielding 0.9 g of compound (220).

Example B.27

A mixture of compound (171) (0.015 mol) in THF (30 ml) was cooled to 0° C. Sodiumhydride (60% in oil) (0.015 mol) was added portionwise. Dimethyl sulfate (0.0165 mol) was added dropwise. The mixture was stirrred from 0° C. to room temperature for 4 hours, poured out into water and extracted with DCM. The organic layer was separated, dried, filtered, and the solvent was evaporated. The residue was purified by column chromatography over silica gel (eluent: $CH_2Cl_2/CH_3OH/NH_4OH$; 95/5/0.1), yielding 4.5 g of compound (175).

Example B.28

A mixture of carbamodithioic acid 4-[[[hexahydro-1-(phenylmethyl)-1H-azepin-4-yl]carbonyl]amino]-3-pyridinyl diethyl ester (0.00876 mol) in formic acid (50 ml) was stirred at 100° C. for 3 hours. The solvent was evaporated. The residue was poured out on ice, basified with $K_2CO_3$ (powder) and extracted with ethyl acetate. The organic layer was separated, dried, filtered and the solvent was evaporated. The residue was dissolved in 2-propanone and converted into hydrochloric acid salt. The precipitate was filtered off and dried, yielding: 1.16 g of compound (215) (mp. 184° C.).

Example B.29

2-Benzofurancarboxaldehyde (0.00915 mol) then $NaBH_3CN$ (0.001 mol) were added at room temperature to a mixture of compound (87) (0.0083 mol) in ACN (100 ml). Acetic acid (1.8 ml) was added at room temperature. The mixture was stirred at room temperature for 2 hours, poured out into $K_2CO_3$ (10%) and extracted with ethyl acetate. The organic layer was separated, dried, filtered, and the solvent was evaporated till dryness. The residue was taken up in methanol in 10 ml of 2-propanol/HCl (5N). The mixture was stirred and refluxed overnight. the solvent was evaporated till dryness. The residue was taken up in $K_2CO_3$ (10%). The mixture was extracted with DCM. The organic layer was separated, dried, filtered, and the solvent was evaporated till dryness. The residue was purified by column chromatography over silica gel (eluent: $CH_2Cl_2/CH_3OH/NH_4OH$; 95/5/0.2;2-propanone/$CH_3CN$. The precipitate was filtered off and dried, yielding 0.9 g of compound (236) (mp. 125° C.).

Tables F-1 to F-6 list the compounds that were prepared according to one of the above Examples. The following abbreviations were used in the tables: .$C_2H_2O_4$ stands for the ethanedioate salt.

TABLE 1

| Co. No. | Ex. No. | $R^1$ | $R^2$ | $R^3$ | $R^a$ | $R^b$ | Physical data |
|---|---|---|---|---|---|---|---|
| 1 | B.3 | phenyl-methyl | OH | 4-fluoro-phenylmethyl | H | H | — |
| 2 | B.4 | H | OH | 4-fluoro-phenylmethyl | H | H | •$H_2O$ (2:1); mp. 160.3° C. |
| 3 | B.4 | H | H | 4-fluoro-phenylmethyl | H | H | •$C_2H_2O_4$ (1:2); mp. 129.7° C. |
| 4 | B.4 | $CH_3$ | OH | 4-fluoro-phenylmethyl | H | H | mp. 127.2° C. |
| 5 | B.5 | 4-methoxy-phenylethyl | OH | 4-fluoro-phenylmethyl | H | H | •(E)-2-butenedioate (1:1); mp. 232.2° C. |
| 6 | B.3 | phenylmethyl | OH | H | H | H | mp. 150.5° C. |
| 7 | B.3 | $CH_3CH_2OCO$— | OH | H | H | H | mp. 228.1° C. |
| 8 | B.4 | H | H | H | H | H | mp. 252.3° C. |
| 9 | B.5 | $(CH_3)_3CO$—CO— | H | H | H | H | mp. 215.5° C. |
| 10 | B.3 | 4-methoxy-phenylethyl | OH | H | H | H | mp. 176° C. |
| 11 | B.3 | $CH_3$ | OH | H | H | H | mp. 216° C. |
| 12 | B.11 | phenylmethyl | H | H | H | H | mp. 220° C. |
| 13 | B.11 | 4-methoxy-phenylethyl | H | H | H | H | mp. 163° C. |
| 14 | B.11 | $CH_3$ | H | H | H | H | mp. >260° C. |
| 15 | B.3 | phenylmethyl | OH | H | $CH_3$ | $CH_3$ | — |
| 16 | B.3 | phenylmethyl | OH | H | Cl | Cl | — |
| 17 | B.3 | phenylmethyl | OH | H | Cl | Cl | •HCl(1:2); mp. 152° C. |
| 18 | B.3 | $CH_3CH_2OCO^-$ | OH | H | $CH_3$ | $CH_3$ | — |
| 19 | B.3 | $CH_3CH_2OCO$— | OH | H | Cl | Cl | — |
| 20 | B.3 | 3-chloro-phenylmethyl | OH | H | H | H | — |
| 21 | B.3 | phenylmethyl | OH | H | $CH_3O$ | $CH_3O$ | — |
| 22 | B.3 | 4-chloro-phenylmethyl | OH | H | H | H | — |
| 23 | B.3 | 2-chloro-phenylmethyl | OH | H | H | H | — |
| 24 | B.3 | phenylethyl | OH | H | H | H | — |
| 25 | B.3 | $CH_3CH_2OCO$— | OH | H | $CH_3O$ | $CH_3O$ | — |
| 26 | B.1 | phenylmethyl | H | $CH_3$ | H | H | •HCl(1:2)•$H_2O$(1:1); mp. 170° C. |
| 27 | B.9 | phenylmethyl | H | phenyl-CO—$CH_2$ | H | H | mp. 138° C. |
| 28 | B.9 | phenylmethyl | H | phenyl-methyl | H | H | •HCl(1:2)•$H_2O$(1:1); mp. 190° C. |
| 29 | B.12 | phenylmethyl | H | phenyl-CH(OH)—$CH_2$ | H | H | •$C_2H_2O_4$ (1:2); mp. 115° C. |
| 171 | B.1 | phenylmethyl | H | H | $CH_3$ | $CH_3$ | mp. 114° C. |
| 172 | B.4 | H | H | H | $CH_3$ | $CH_3$ | mp. 138° C. |
| 173 | B.1 | phenylmethyl | H | H | $CH_3$ | H | •$C_2H_2O_4$ (2:3); mp. 114° C. |
| 174 | B.4 | H | H | H | $CH_3$ | H | mp. 206° C. |
| 175 | B.27 | phenylmethyl | H | $CH_3$ | $CH_3$ | $CH_3$ | — |
| 176 | B.4 | H | H | $CH_3$ | $CH_3$ | $CH_3$ | •HCl (1:2)•$H_2O$ (1:1); mp. 248° C. |

TABLE 2

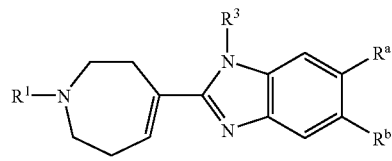

| Co. No. | Ex. No. | R¹ | R³ | Rᵃ | Rᵇ | Physical data |
|---|---|---|---|---|---|---|
| 30 | B.6 | phenylmethyl | 4-fluoro-phenylmethyl | H | H | — |
| 31 | B.6 | phenylmethyl | H | H | H | mp. 221.9° C. |
| 32 | B.6 | 4-methoxy-phenylethyl | H | H | H | mp. 152° C. |
| 33 | B.6 | CH₃ | H | H | H | mp. 208° C. |
| 34 | B.6 | H | H | H | H | •HCl(1:2); mp. 260° C. |
| 35 | B.6 | phenylmethyl | H | CH₃ | CH₃ | mp. 222° C. |
| 36 | B.6 | phenylmethyl | H | Cl | Cl | mp. 197° C. |
| 37 | B.6 | H | H | CH₃ | CH₃ | •HCl (1:2) •H₂O (1:1) |
| 38 | B.6 | H | H | Cl | Cl | mp. 196° C. |
| 39 | B.6 | 3-chloro-phenylmethyl | H | H | H | mp. 202° C. |
| 40 | B.6 | 4-chloro-phenylmethyl | H | H | H | mp. 217° C. |
| 41 | B.6 | 2-chloro-phenylmethyl | H | H | H | mp. 195° C. |
| 42 | B.6 | phenylethyl | H | H | H | mp. 158° C. |
| 43 | B.6 | phenylmethyl | H | CH₃O | CH₃O | mp. 186° C. |
| 44 | B.14 | H | H | CH₃O | CH₃O | •C₂H₂O₄ (1:2); mp. >250° C. |
| 45 | B.6 | H | H | H | H | — |
| 46 | B.5 | benzoyl | H | H | H | mp. 191° C. |
| 47 | B.9 | phenylmethyl | phenylmethyl | H | H | mp. 100° C. |
| 48 | B.9 | phenylmethyl | phenylCO—CH₂ | H | H | mp. 166° C. |
| 49 | B.9 | phenylmethyl | CH₃ | H | H | •C₂H₂O₄ (1:2); mp. 172° C. |
| 50 | B.9 | phenylmethyl | CH₃CH₂ | H | H | mp. 92° C. |

TABLE 3

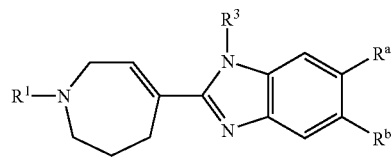

| Co. No. | Ex. No. | R¹ | R³ | Rᵃ | Rᵇ | Physical data |
|---|---|---|---|---|---|---|
| 51 | B.6 | phenylmethyl | 4-fluoro-phenylmethyl | H | H | — |
| 52 | B.6 | phenylmethyl | H | H | H | mp. 176.4° C. |
| 53 | B.6 | 4-methoxy-phenylethyl | H | H | H | mp. 144° C. |
| 54 | B.6 | CH₃ | H | H | H | mp. 196° C. |
| 55 | B.6 | H | H | H | H | mp. 218° C. |
| 56 | B.6 | phenylmethyl | H | CH₃ | CH₃ | mp. 178° C. |
| 57 | B.6 | phenylmethyl | H | Cl | Cl | mp. 158° C. |
| 58 | B.6 | H | H | CH₃ | CH₃ | •HCl (1:2) •H₂O (1:1) |
| 59 | B.6 | H | H | Cl | Cl | mp. 234° C. |
| 60 | B.6 | 3-chloro-phenylmethyl | H | H | H | mp. 160° C. |
| 61 | B.6 | 4-chloro-phenylmethyl | H | H | H | mp. 148° C. |
| 62 | B.6 | 2-chloro-phenylmethyl | H | H | H | mp. 60° C. |
| 63 | B.6 | phenylethyl | H | H | H | mp. 166° C. |
| 64 | B.6 | phenylmethyl | H | CH₃O | CH₃O | •C₂H₂O₄ (1:2) mp. 220° C. |
| 65 | B.6 | CH₃CH₂OCO— | H | CH₃O | CH₃O | — |
| 66 | B.14 | H | H | CH₃O | CH₃O | •C₂H₂O₄ (1:2) •H₂O (1:1); mp. 95° C. |
| 67 | B.9 | phenylmethyl | phenylmethyl | H | H | mp. 80° C. |
| 68 | B.9 | phenylmethyl | phenyl-CO—CH₂ | H | H | mp. 130° C. |

TABLE 4
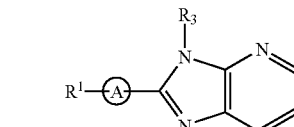
| Co. No. | Ex. No. | R¹ | —(A)— | R³ | Physical data |
|---|---|---|---|---|---|
| 69 | B.1 | phenylmethyl | 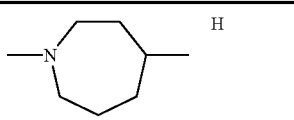 | H | mp. 138° C. |
| 71 | B.4 | H | 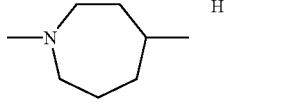 | H | •HCl (1:2); mp. 238° C. |
| 72 | B.3 | phenylmethyl | 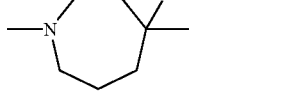 | $(CH_3)_2NSO_2$— | — |
| 73 | B.1 | phenylmethyl |  | H | mp. 150° C. |
| 74 | B.1 | phenylmethyl | 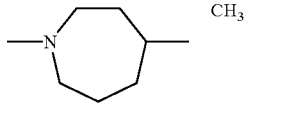 | $CH_3$ | •HCl (1:2); mp 202° C. |
| 75 | B.9 | phenylmethyl | 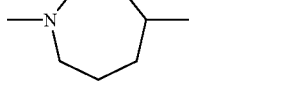 | phenylmethyl | •HCl(1:2)•$H_2O$(1:1); mp. 130° C. |
| 76 | B.9 | phenylmethyl | 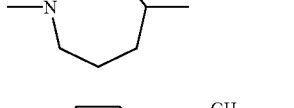 | phenylCOCH₂— | •HCl (1:2); mp. 150° C. |
| 77 | B.1 | phenylmethyl | 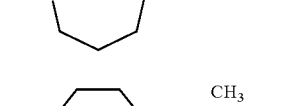 | $CH_3$ | — |
| 78 | B.4 | H | 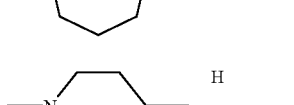 | $CH_3$ | •HCl(1:2)•$H_2O$(1:1); mp. 192° C. |
| 79 | B.4 | H | 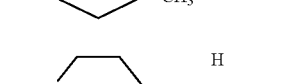 | H | •HCl(1:2); mp. 190° C. |
| 80 | B.2 | phenylmethyl |  | H | (A); $[\alpha]_D^{20}$ = −15.08° (c = 8.49 mg/1 ml in methanol); mp. 140° C. |

TABLE 4-continued

| Co. No. | Ex. No. | R¹ | —(A)— | R³ | Physical data |
|---|---|---|---|---|---|
| 81 | B.2 | phenylmethyl | 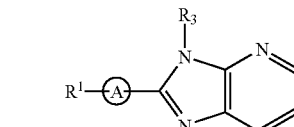 | H | (B); $[\alpha]_D^{20}$ = 15.52° (c = 8.70 mg/1 ml in methanol) mp. 138° C. |
| 82 | B.9 | phenylmethyl | 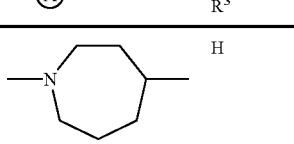 | phenylmethyl | •$C_2H_2O_4$(1:1); mp. 197° C. |
| 83 | B.1 | 2-chloro-phenylmethyl | 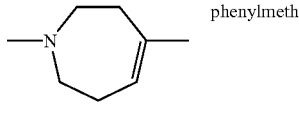 | H | •$C_2H_2O_4$(1:1), mp. 212° C. |
| 84 | B.5 | phenylcarbonyl | 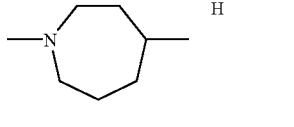 | H | •HCl(1:2); mp. 94° C. |
| 85 | B.1 | 3-chloro-phenylmethyl | 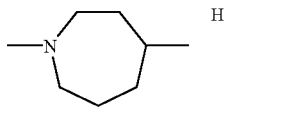 | H | •$C_2H_2O_4$(2:3); mp. 228° C. |
| 86 | B.1 | 4-pyridinyl-methyl | 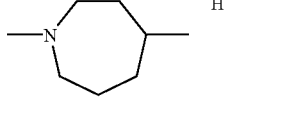 | H | •HCl(1:3); mp. 272° C. |
| 87 | B.4 | H | 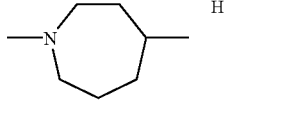 | H | — |
| 88 | B.5 | 4-fluoro-phenylmethyl | 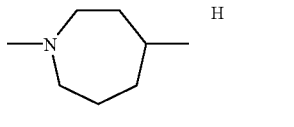 | H | mp. 118° C. |
| 89 | B.5 | 3,4-dichloro-phenylmethyl | 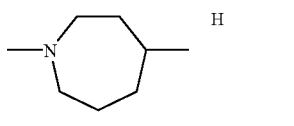 | H | mp. 120° C. |
| 90 | B.5 | 4-methyl-phenylmethyl | 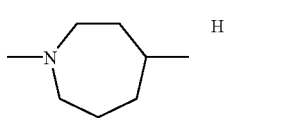 | H | mp. 144° C. |
| 91 | B.5 | CH₃—CO— | 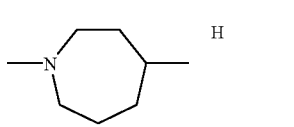 | H | •HCl(1:1); mp. 199° C. |

TABLE 4-continued

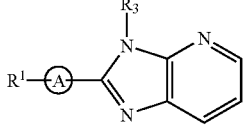

| Co. No. | Ex. No. | R¹ | —Ⓐ— | R³ | Physical data |
|---|---|---|---|---|---|
| 92 | B.5 | 4-nitro-phenylmethyl | 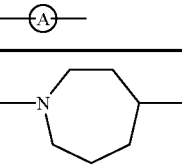 | H | mp. 154° C. |
| 93 | B.5 | 2-pyridinyl-methyl | 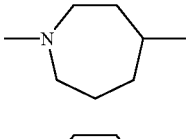 | H | mp. 115° C. |
| 94 | B.5 | phenyl-SO₂— | 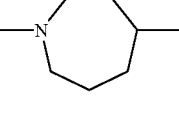 | H | mp. 202° C. |
| 95 | B.5 | CH₃—SO₂— | 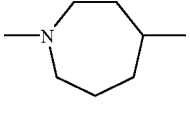 | H | mp. 220° C. |
| 96 | B.5 | CF₃—CO— | 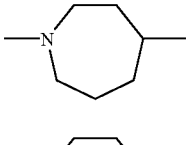 | H | (A); $[\alpha]_D^{20}$ = −29.38° (c = 8.51 mg/1 ml in methanol); mp. 165° C. |
| 97 | B.5 | CF₃—CO— | 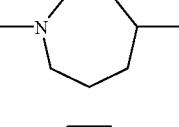 | H | (B); $[\alpha]_D^{20}$ = 28.37 (c = 9.13 mg/1 ml in methanol); mp. 165° C. |
| 98 | B.5 | 2-naphthalenyl-methyl | 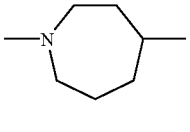 | H | mp. 101° C. |
| 99 | B.5 | 3,4-dimethyl-methyl | 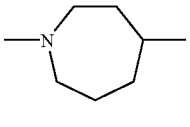 | H | mp. 112° C. |
| 100 | B.5 | 2-quinolinyl-methyl | 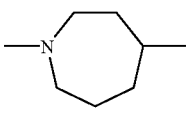 | H | mp. 131° C. |
| 101 | B.5 | 4-methoxy-phenylmethyl | 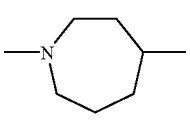 | H | mp. 136° C. |
| 102 | B.4 | H | 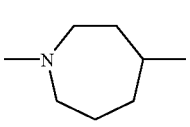 | H | (A); $[\alpha]_D^{20}$ = 19.16° (c = 11.17 mg/2 ml in 1 N HCl); mp. 164° C. |

TABLE 4-continued

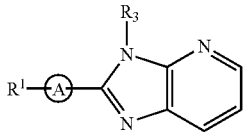

| Co. No. | Ex. No. | R¹ | —(A)— | R³ | Physical data |
|---|---|---|---|---|---|
| 103 | B.1 | phenyl-methyl | 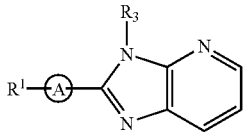 | H | •(Z)-2-butenedioate (1:2) |
| 104 | B.1 | phenylmethyl | 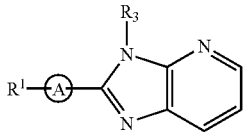 | H | .2-hydroxy-1,2,3-propanetri-carboxylate(1:1)•H₂O(1:1); mp. 100° C. |
| 105 | B.16 | 4-amino-phenylmethyl | 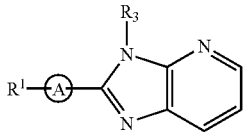 | H | — |
| 106 | B.2 | phenylmethyl | 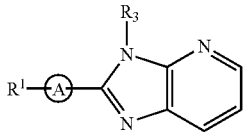 | H | .(Z)-2-butenedioate (1:1); (B); [α]$_D^{20}$ = 18.02° (c = 10.43 mg/2 ml in methanol); mp. 149° C. |
| 107 | B.4 | H | 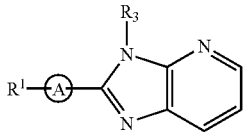 | H | (B); [α]$_D^{20}$ = −17.77° (c = 9.68 mg/2 ml in 1 N HCl); mp. 163° C. |
| 108 | B.2 | phenylmethyl | 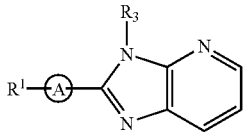 | H | (B); [α]$_D^{20}$ = 18.83° (c = 11.47 mg/2 ml in methanol); 2-hydroxy-1,2,3-propane-tricarboxylate(1:1) H₂O(1:1) |
| 109 | B.1 | phenylmethyl | 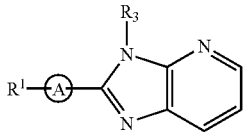 | H | •(E)-2-butenedioate (1:1); mp. 190° C. |
| 110 | B.1 | phenylmethyl | 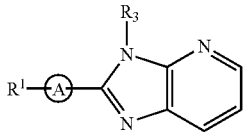 | H | •HBr(1:2)•H₂O(1:1); mp. 240° C. |
| 111 | B.3 | CH₃CH₂OCO— | 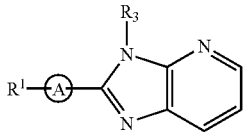 | (CH₃)₂NSO₂— | — |
| 112 | B.10 | CH₃CH₂OCO— | 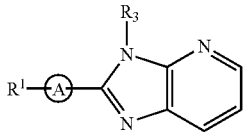 | H | mp. 212° C. |
| 113 | B.8 | phenylmethyl | 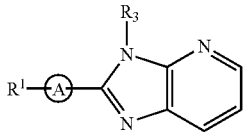 | H | (A); mp. 206° C. |

TABLE 4-continued
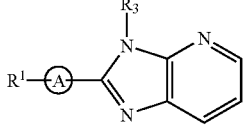
| Co. No. | Ex. No. | R¹ | —(A)— | R³ | Physical data |
|---|---|---|---|---|---|
| 114 | B.8 | phenylmethyl |  | H | (B); mp. 181° C. |
| 115 | B.6 | H | 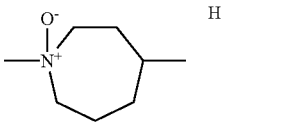 | H | — |
| 116 | B.6 | H | 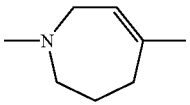 | H | mp. 238° C. |
| 117 | B.5 | 4-methyl-phenylmethyl | 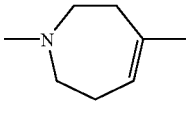 | H | mp. 184° C. |
| 118 | B.17 | 3-pyridinyl-carbonyl | 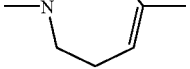 | H | •H₂O(1:1); mp. 100° C. |
| 119 | B.5 | CH₃CO— | 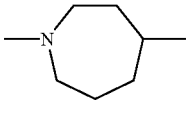 | H | mp. 209° C. |
| 120 | B.5 | 4-fluoro-phenylmethyl | 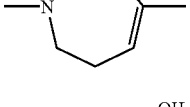 | H | mp. 143° C. |
| 121 | B.6 | 4-fluoro-phenylmethyl | 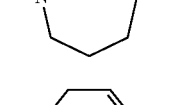 | H | mp. 208° C. |
| 122 | B.6 | 4-fluoro-phenylmethyl | 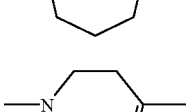 | H | mp. 206° C. |
| 123 | B.3 | 4-fluoro-phenylmethyl | 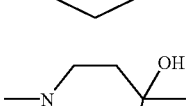 | CH₃SO₂— | — |
| 124 | B.5 | 4-methoxy-phenylmethyl |  | H | mp. 185° C. |

TABLE 4-continued

| Co. No. | Ex. No. | R¹ | —(A)— | R³ | Physical data |
|---|---|---|---|---|---|
| 125 | B.5 | 4-methoxy-phenylmethyl | 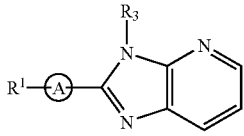 | H | mp. 176° C. |
| 130 | B.5 | phenyl-SO₂— | 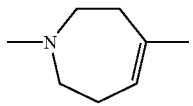 | H | mp. 243° C. |
| 135 | B.5 | 2-naphthalenyl-methyl | 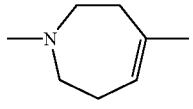 | H | mp. 229° C. |
| 136 | B.5 | (CH₃)₃C—CO— | 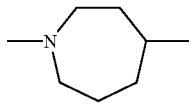 | H | mp. 153° C. |
| 137 | B.2 | phenylmethyl | 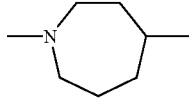 | H | (B); $[\alpha]_D^{20}$ = 25.29° (c = 11.39 mg/2 ml in methanol); •HBr(1:2).H₂O(1:1); mp. 214° C. |
| 138 | B.2 | phenylmethyl | 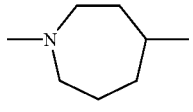 | H | (A); $[\alpha]_D^{20}$ = −21.85° (c = 11.35 mg/2 ml in methanol); •HBr(1:3)•H₂O(1:1); mp. 170° C. |
| 139 | B.5 | 1,3-benzo-dioxoyl-methyl | 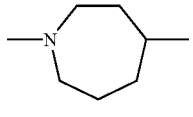 | H | mp. 60° C. |
| 140 | B.5 | phenylmethyl-carbonyl | 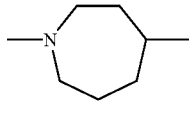 | H | mp. 55° C. |
| 177 | B.5 | phenylethyl- | 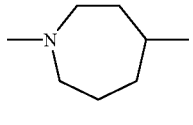 | H | mp. 111° C. |
| 178 | B.5 | 2,3-dimethyl-phenylmethyl | 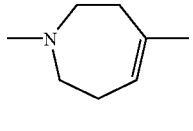 | H | mp. 161° C. |
| 179 | B.5 | 3,4-dimethyl-phenylmethyl | 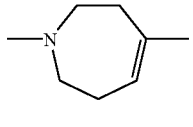 | H | mp. 187° C. |

TABLE 4-continued
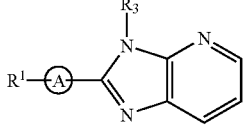
| Co. No. | Ex. No. | R¹ | —Ⓐ— | R³ | Physical data |
|---|---|---|---|---|---|
| 180 | B.18 | CH₃—SO₂— | 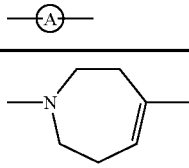 | H | mp. >260° C. |
| 181 | B.5 | 2-pyridinyl-methyl- | 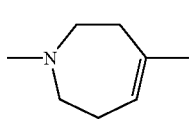 | H | mp. 175° C. |
| 182 | B.19 | phenylmethyl-carbonyl | 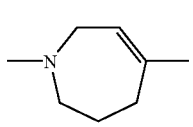 | H | mp. 169° C. |
| 183 | B.19 | phenylmethyl-carbonyl | 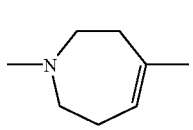 | H | mp. 157° C. |
| 184 | B.1 | phenyl | 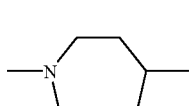 | H | mp. 175° C. |
| 185 | B.17 | 2-pyridinyl-carbonyl | 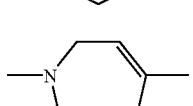 | H | mp. 171° C. |
| 186 | B.17 | 3-pyridinyl-carbonyl | 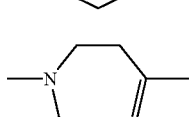 | H | mp. 182° C. |
| 187 | B.20 | ethoxycarbonyl | 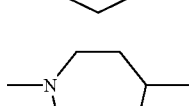 | ethoxycarbonyl | — |
| 188 | B.21 | ethoxycarbonyl | 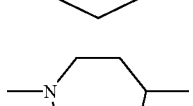 | H | mp. 141° C. |
| 189 | B.5 | 3-methoxy-phenylmethyl | 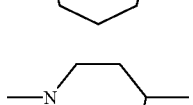 | H | mp. 111° C. |
| 190 | B.3 | phenyl | 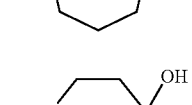 | (CH₃)₂NSO₂— | — |

TABLE 4-continued
| Co. No. | Ex. No. | R¹ | —(A)— | R³ | Physical data |
|---|---|---|---|---|---|
| 191 | B.10 | phenyl | 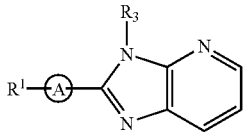 | H | — |
| 192 | B.6 | phenyl | 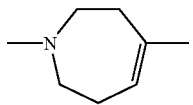 | H | mp. 228° C. |
| 193 | B.5 | 3,4-dichloro-phenylmethyl | 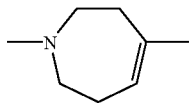 | 3,4-dichloro-phenylmethyl | mp. 99° C. |
| 194 | B.5 | 3,4-dichloro-phenylmethyl | 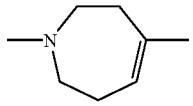 | H | mp. 184° C. |
| 195 | B.24 | phenylmethyl | 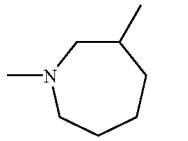 | H | mp. 139° C. |
| 196 | B.5 | 3-pyridinyl-methyl | 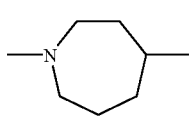 | H | mp. 203° C.; •HCl(1:3).H₂O(1:1) |
| 197 | B.3 | phenylmethyl | 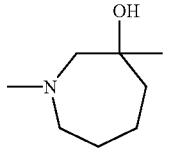 | (CH₃)₂NSO₂— | — |
| 198 | B.5 | 4-cyanophenyl-methyl | 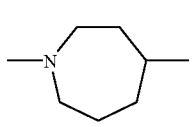 | H | mp. 155° C. |
| 199 | B.5 | 3-cyanophenyl-methyl | 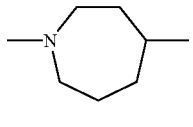 | H | mp. 219° C. |
| 200 | B.5 | 2-cyanophenyl-methyl | 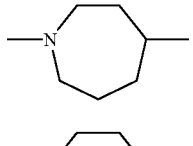 | H | mp. 172° C.; •C₂H₂O₄(1:2) |
| 201 | B.5 | 4-cyanophenyl-methyl | 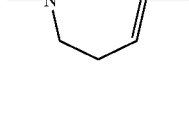 | H | mp. 241° C. |

TABLE 4-continued
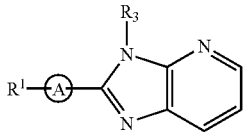
| Co. No. | Ex. No. | R¹ | —Ⓐ— | R³ | Physical data |
|---|---|---|---|---|---|
| 232 | B.5 | 2-furanyl | 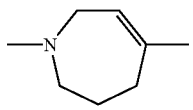 | H | mp. 128° C. |
| 233 | B.5 | 2-furanyl | 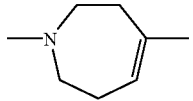 | H | mp. 169° C. |
| 234 | B.19 | phenyloxy-carbonyl | 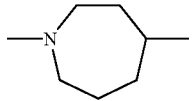 | H | mp. 136° C. |
| 235 | B.19 | phenylmethyl-oxycarbonyl | 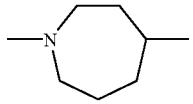 | H | mp. 124° C. |
| 236 | B.29 | 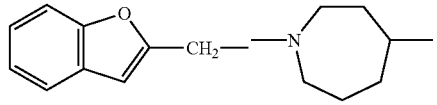 | 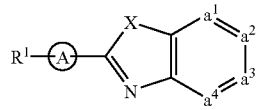 | H | mp. 125° C. |
TABLE 5
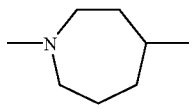
| Co. No. | Ex. No. | R¹ | —Ⓐ— | X | —a¹=a²—a³=a⁴— | Physical data |
|---|---|---|---|---|---|---|
| 141 | B.1 | phenylmethyl | 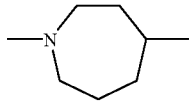 | O | —CH=CH—CH=CH— | mp. 176° C. |
| 142 | B.1 | phenylmethyl | 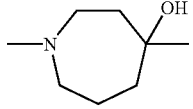 | N—H | —CH=CH—N=CH— | mp. 114° C. |
| 143 | B.3 | phenylmethyl | 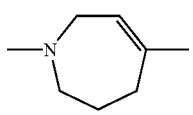 | N—SO₂—N(CH₃)₂ | —CH=CH—CH=N— | — |
| 144 | B.6 | phenylmethyl |  | N—H | —CH=CH—CH=N— | mp. 170° C. |

TABLE 5-continued

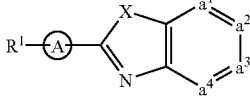

| Co. No. | Ex. No. | R¹ | —Ⓐ— | X | —a¹=a²—a³=a⁴— | Physical data |
|---|---|---|---|---|---|---|
| 145 | B.6 | phenylmethyl | 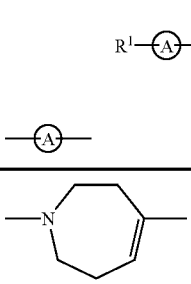 | N—H | —CH=CH—CH=N— | mp. 174° C. |
| 146 | B.1 | phenylmethyl | 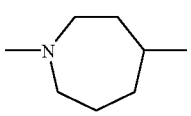 | O | —N=CH—N=C(NH₂)— | •C₂H₂O₄ (1:2) •H₂O(1:1); mp. 105° C. |
| 147 | B.1 | phenylmethyl | 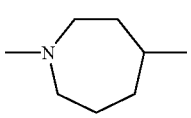 | N—H | —C(CH₃)=CH—CH=N— | mp. 100° C. |
| 148 | B.1 | phenylmethyl | 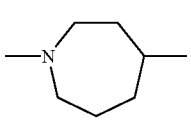 | N—H | —N=CH—N=C(OH)— | •C₂H₂O₄ (1:1) .H₂O(1:2); mp. 150° C. |
| 149 | B.10 | phenylmethyl | 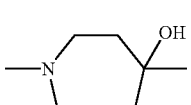 | N—H | —CH=CH—CH=N— | mp. 159° C. |
| 150 | B.1 | phenylmethyl | 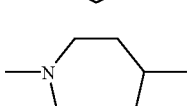 | O | —CH=CH—CH=N— | •C₂H₂O₄ (1:1); mp. 80° C. |
| 151 | B.1 | phenylmethyl | 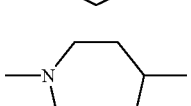 | N—H | —CH=C(Br)—CH=N— | mp. 167° C. |
| 152 | B.3 | phenylmethyl | 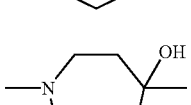 | N—CH₃ | —CH=CH—CH=N— | — |
| 153 | B.6 | phenylmethyl | 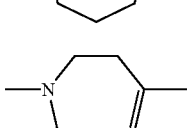 | N—CH₃ | —CH=CH—CH=N— | •HCl(1:3) |
| 154 | B.13 | phenylmethyl | 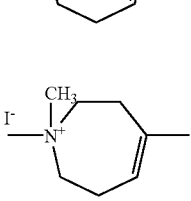 | N—H | —CH=CH—CH=CH— | mp. 168° C. |
| 155 | B.4 | H | 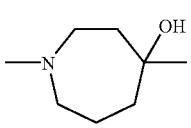 | N—H | —CH=CH—CH=N— | mp. 254° C. |

TABLE 5-continued

| Co. No. | Ex. No. | R¹ | —(A)— | X | —a¹=a²—a³=a⁴— | Physical data |
|---|---|---|---|---|---|---|
| 156 | B.5 | CH₃SO₂— |  | N—SO₂—CH₃ | —CH=CH—CH=N— | mp. 207° C. |
| 157 | B.3 | CH₃CH₂O(CO)— | 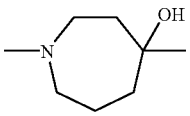 | NSO₂—(N(CH₃)₂) | —CH=CH—CH=N— | — |
| 158 | B.3 | 4-fluoro-phenylmethyl | 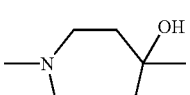 | NSO₂(N(CH₃)₂) | —CH=CH—CH=N— | — |
| 159 | B.3 | phenylmethyl | 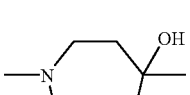 | NSO₂N(CH₃)₂ | —CH=C(Br)—CH=N— | — |
| 160 | B.1 | phenylmethyl | 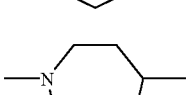 | N—H | —N=CH—CH=N— | mp. 198° C. |
| 161 | B.7 | (CH₃)₃C(CO)— | 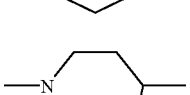 | N—H | —N⁺(O⁻)=CH—CH=CH— | mp. >260° C. |
| 162 | B.14 | H | 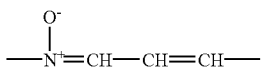 | NH | —N⁺(O⁻)=CH—CH=CH— | •H₂O (1:2) |
| 163 | B.5 | phenylmethyl | 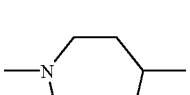 | N—H | —N⁺(O⁻)=CH—CH=CH— | mp. 149° C. |
| 202 | B.6 | phenylmethyl | 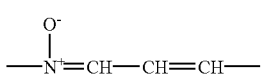 | NH | —C(CH₃)=CH—CH=N— | mp. 220° C. |
| 203 | B.3 | phenylmethyl | 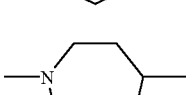 | NSO₂N(CH₃)₂ | —CH=C(CH₂CH₃)—C(CH₃)=N— | — |
| 204 | B.15 | phenylmethyl | 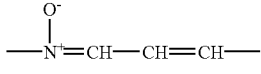 | N—H | —C(OH)=CH—CH=N— | mp. >260° C. |

TABLE 5-continued

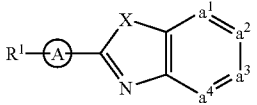

| Co. No. | Ex. No. | R¹ | —(A)— | X | —a¹=a²—a³=a⁴— | Physical data |
|---|---|---|---|---|---|---|
| 205 | B.5 | phenylethyl | 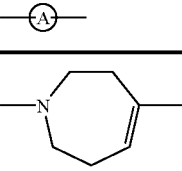 | N—H | —CH=CH—CH=N— | mp. 195° C. |
| 206 | B.15 | 4-hydroxy-phenyl |  | N—H | —CH=CH—CH=N— | mp. 118° C. |
| 207 | B.1 | phenylmethyl |  | S | —CH=CH—CH=CH— | •C₂H₂O₄ (1:1); mp. 141° C. |
| 208 | B.3 | phenyl | 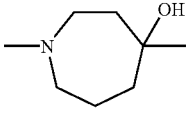 | NSO₂N(CH₃)₂ | —CH=CH—CH=N— | — |
| 209 | B.13 | phenylmethyl | 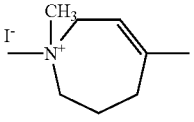 | N—H | —CH=CH—CH=CH— | mp. 172° C. |
| 210 | B.3 | phenylmethyl | 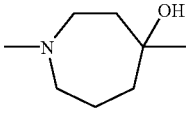 | S | —CH=CH—CH=CH— | mp. 90° C. |
| 211 | B.10 | phenylmethyl | 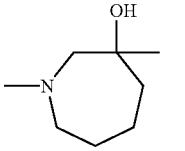 | N—H | —CH=CH—CH=N— | — |
| 212 | B.6 | phenylmethyl | 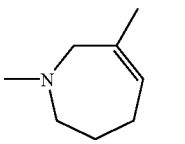 | N—H | —CH=CH—CH=N— | mp. 191° C. |
| 213 | B.23 | phenylmethyl | 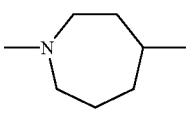 | O | —N=CH—CH=CH— | •C₂H₂O₄ (1:1); mp. 102° C. |
| 214 | B.6 | phenylmethyl | 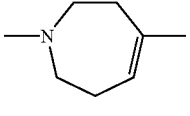 | S | —CH=CH—CH=CH— | mp. 84° C. |

TABLE 5-continued

| Co. No. | Ex. No. | R¹ | —(A)— | X | —a¹=a²—a³=a⁴— | Physical data |
|---|---|---|---|---|---|---|
| 215 | B.28 | phenylmethyl | 4-methylazepan-1-yl (N-linked) | S | —CH=N—CH=CH— | •HCl (1:2); mp. 184° C. |
| 216 | B.13 | phenylmethyl | N-methyl-4-methyl-2,3,6,7-tetrahydroazepinium iodide | S | —CH=CH—CH=CH— | .H₂O (1:1); mp. 161° C. |
| 217 | B.22 | phenylmethyl | 4-methylazepan-1-yl | N—H | —CH=C(COOCH₃)—CH=N— | mp. 150° C. |
| 218 | B.25 | phenylmethyl | 4-methylazepan-1-yl | S | —N=CH—CH=CH— | •C₂H₂O₄ (1:1); mp. 163° C. |
| 219 | B.13 | phenylmethyl | N-methyl-4-methyl-2,3,6,7-tetrahydroazepinium iodide | N—H | —CH=CH—CH=N— | mp. >260° C. |
| 220 | B.26 | H | 4-methylazepan-1-yl | S | —CH=CH—CH=CH— | — |
| 221 | B.5 | 1,3-benzo-dioxoyl-methyl | 4-methylazepan-1-yl | S | —CH=CH—CH=CH— | •C₂H₂O₄ (1:1) |
| 222 | B.1 | phenylmethyl | 4-methylazepan-1-yl | N—H | —C(CH₃)=CH—C(CH₃)=CH— | •C₂H₂O₄ (1:2); mp. 224° C. |
| 223 | B.4 | H | 4-methylazepan-1-yl | N—H | —C(CH₃)=CH—C(CH₃)=CH— | •HCl (1:2). .H₂O (1:1); mp. 228° C. |
| 224 | B.4 | H | 4-methylazepan-1-yl | N—H | —C(OH)=CH—CH=N— | •HCl (1:2); mp. 200° C. |
| 225 | B.26 | H | 4-methylazepan-1-yl | S | —CH=CH—CH=CH— | •HCl (1:1); mp. 210° C. |

TABLE 6
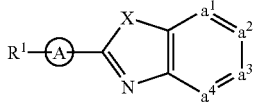
| Co. No. | Ex. No. | R¹ | —(A)— | 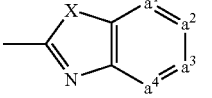 | Physical data |
|---|---|---|---|---|---|
| 164 | B.1 | phenylmethyl | 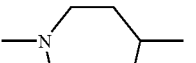 | 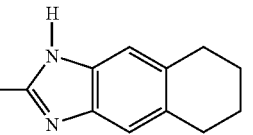 | mp. 162° C. |
| 165 | B.4 | H | 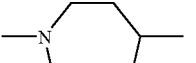 | 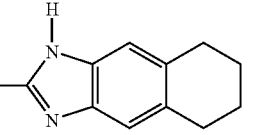 | mp. 230° C. |
| 166 | B.3 | phenylmethyl | 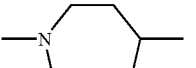 | 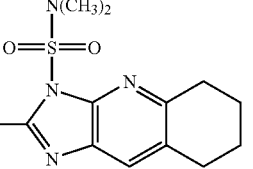 | — |
| 167 | B.3 | phenylmethyl |  | 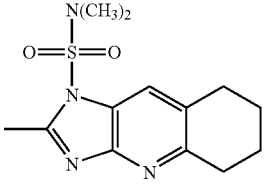 | — |
| 168 | B.10 | phenylmethyl | 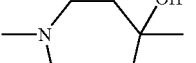 | 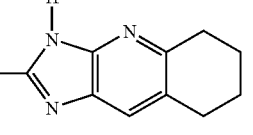 | — |
| 169 | B.6 | phenylmethyl | 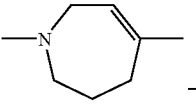 | 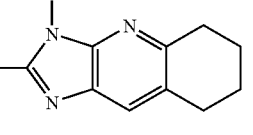 | — |
| 170 | B.6 | phenylmethyl | 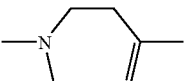 | 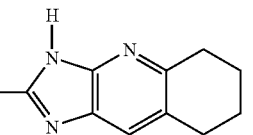 | — |

TABLE 7
| Co. No. | Ex. No. | A | R³ | Rᵃ | Rᵇ | Rᶜ | Physical data |
|---|---|---|---|---|---|---|---|
| 70 | B.1 | 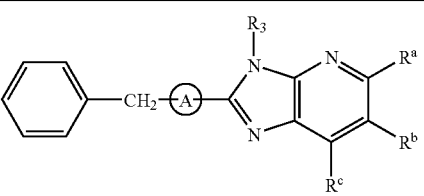 | H | CH₃ | CH₂CH₃ | H | ·HCl (1:2) ·H₂O (1:1); mp. >120° C. |
| 126 | B.1 | 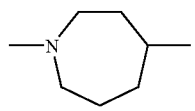 | H | CH₃O | H | H | mp. 126° C. |
| 127 | B.15 | 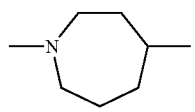 | H | OH | H | H | mp. 118° C. |
| 128 | B.15 | 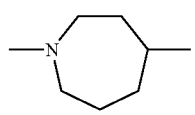 | H | H | OH | H | mp. 226° C. |
| 129 | B.1 | 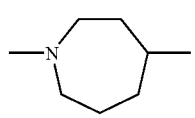 | H | H | OCH₃ | H | mp. 173° C. |
| 131 | B.3 | 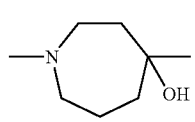 | (CH₃)₂NSO₂— | H | Br | H | — |
| 132 | B.10 | 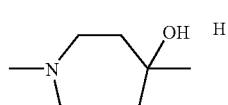 | H | H | Br | H | mp. 183° C. |
| 133 | B.6 | 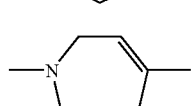 | H | H | Br | H | — |
| 134 | B.6 | 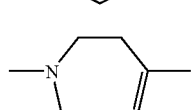 | H | H | Br | H | mp. 233° C. |
| 226 | B.3 | 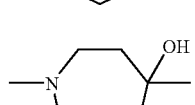 | (CH₃)₂NSO₂— | H | H | CH₃ | — |
| 227 | B.6 | 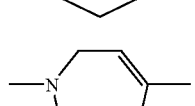 | H | CH₃ | CH₂CH₃ | H | mp. 173° C. |

TABLE 7-continued

[Structure: phenyl-CH2-(A)-imidazo[4,5-b]pyridine with R3 on N, Ra, Rb, Rc substituents]

| Co. No. | Ex. No. | —(A)— | R³ | Rᵃ | Rᵇ | Rᶜ | Physical data |
|---|---|---|---|---|---|---|---|
| 228 | B.6 | azepinyl (with double bond) | H | $CH_3$ | $CH_2CH_3$ | H | mp. 161° C. |
| 229 | B.3 | 4-OH-azepanyl | $(CH_3)_2NSO_2$— | $CH_3$ | $CH_2CH_3$ | H | — |
| 230 | B.10 | 4-OH-azepanyl | H | $CH_3$ | $CH_2CH_3$ | H | mp. 144° C. |
| 231 | B.22 | azepanyl | H | H | H | $CH_3O$— | mp. 124° C. |

C. PHARMACOLOGICAL EXAMPLES

C.1. Gastric Tone Measured by an Electronic Barostat in Conscious Dogs

Gastric tone cannot be measured by manometric methods. Therefore an electronic barostat was used. This allows the study of the physiological pattern and regulation of gastric tone in conscious dogs and the influence of test-compounds on this tone.

The barostat consists of an air injection system which is connected by a double-lumen 14-French polyvinyl tube to an ultrathin flaccid polyethylene bag (maximal volume: ±700 ml). Variations in gastric tone were measured by recording changes in the volume of air within an intragastric bag, maintained at a constant pressure. The barostat maintains a constant pressure (preselected) within a flaccid air-filled bag introduced into the stomach, changing the volume of air within the bag by an electronic feedback system.

Thus, the barostat measures gastric motor activity (contraction or relaxation) as changes in intragastric volume (decrease or increase resp.) at a constant intragastric pressure. The barostat consists of a strain gauge linked by an electronic relay to an air injection-aspiration system Both the strain gauge and the injection system are connected by means of double-lumen polyvinyl tube to an ultrathin polyethylene bag. A dial in the barostat allows selection of the pressure level to be maintained within the intragastric bag.

Female beagle dogs, weighing 7-17 kg, were trained to stand quietly in Pavlov frames. They were implanted with a gastric cannula under general anaesthesia and aseptic precautions. After a median laparotomy, an incision was made through the gastric wall in longitudinal direction between the greater and the lesser curve, 2 cm above the nerves of Latarjet. The cannula was secured to the gastric wall by means of a double purse string suture and brought out via a stub wound at the left quadrant of the hypochondrium Dogs were allowed a recovery period of two weeks.

At the beginning of the experiment, the cannula was opened in order to remove any gastric juice or food remnants. If necessary, the stomach was cleansed with 40 to 50 ml lukewarm water. The ultrathin bag of the barostat was positioned into the fundus of the stomach through the gastric cannula. In order to ensure easy unfolding of the intragastric bag during the experiment, a volume of 150-200 ml was injected into the bag by raising the pressure to maximally 14 mm Hg (about 1.87 kPa) very briefly. This procedure was repeated twice.

After a stabilization period of 60 minutes at an intragastric pressure of 6 mmHg (about 0.81 kPa), the test compound was administered subcutaneously, or intraduodenally, at 2 mmHg (0.27 kPa). Test compounds were screened, i.e. changes in gastric volume are measured, at 0.63 mg/kg s.c. Other doses and routes were tested if a test compound was shown to be active during the screening procedure. Table C-1 summarizes the mean maximal change in volume (in ml) on relaxation of the fundus, 1 hour after S.C. administration of the test compound (0.63 mg/kg).

TABLE C-1

| Co. No. | Maximum change in volume (mean) |
|---|---|
| 35 | 272 |
| 69 | 87 |
| 80 | 55 |
| 81 | 183 |
| 122 | 138 |
| 124 | 49 |
| 125 | 222 |
| 130 | 35 |
| 133 | 61 |
| 145 | 160 |
| 154 | 54 |
| 169 | 53 |
| 170 | 31 |

What is claimed is:

1. A compound of formula (I)

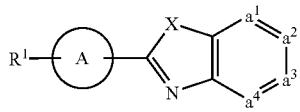

their N-oxides, addition salts, quaternary amines and stereochemically isomeric forms thereof, wherein

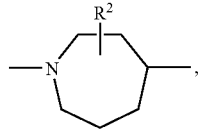 is

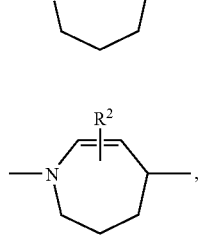 (a-1),

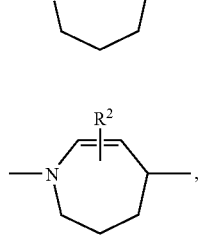 (a-2),

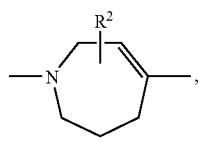 (a-3),

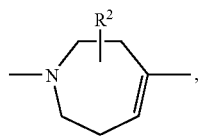 (a-4),

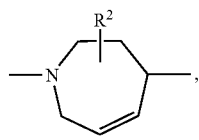 (a-5),

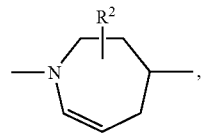 (a-6),

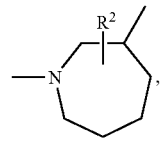 (a-7),

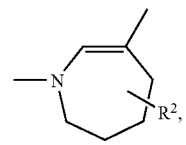 (a-8),

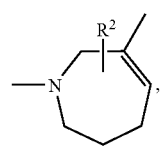 (a-9),

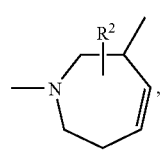 (a-10),

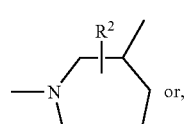 (a-11) or,

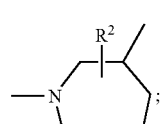 (a-12);

wherein $R^2$ is hydrogen, hydroxy, $C_{1-4}$alkyl, or $C_{1-4}$alkyloxy, and when $R^2$ is hydroxy or $C_{1-4}$alkyloxy then said $R^2$ is bonded at a different position than the α-position of the ring nitrogen, or when $R^2$ is hydroxy then said $R^2$ is bonded at a different position than a vinylic position of radical (a-2), (a-3), (a-4), (a-5), (a-6), (a-8), (a-9), (a-10), (a-11), or (a-12);

-$a^1$=$a^2$-$a^3$=$a^4$- represents a bivalent radical of formula

—CH=CH—CH=CH— (b-1),

—N=CH—CH=CH— (b-2),

—CH=N—CH=CH— (b-3),

—CH=CH—N=CH— (b-4),

—CH=CH—CH=N— (b-5),

—CH=CH—N=N— (b-6),

—N=CH—CH=N— (b-7),

—N=CH—N=CH— (b-8),

—N=N—CH=CH— (b-9),

—CH=N—CH=N— (b-10), or

—CH=N—N=CH— (b-11), wherein each hydrogen atom in the radicals (b-1) to (b-11) may optionally be replaced by halo, $C_{1-6}$alkyl, nitro, amino, hydroxy, $C_{1-6}$alkyloxy, polyhalo$C_{1-6}$alkyl, carboxyl, amino$C_{1-6}$alkyl, hydroxy$C_{1-6}$alkyl, mono- or di($C_{1-4}$alkyl)amino$C_{1-6}$alkyl, $C_{1-6}$alkyloxycarbonyl;

or wherein two hydrogen atoms on adjacent carbon atoms in the radicals (b-1) to (b-11) may optionally be replaced by —(CH$_2$)$_4$—;

$R^1$ is hydrogen, $C_{1-6}$alkyl, aryl$^1$, $C_{1-6}$alkyl substituted with aryl$^1$, $C_{1-4}$alkyloxycarbonyl, aryl$^1$carbonyl, aryl$^1$$C_{1-6}$alkylcarbonyl, aryl$^1$carbonyl$C_{1-6}$alkyl, aryl$^1$oxycarbonyl, aryl$^1$$C_{1-4}$alkyloxycarbonyl, $C_{1-4}$alkylcarbonyl, trifluoromethyl, trifluoromethylcarbonyl, $C_{1-6}$alkylsulfonyl, aryl$^1$sulfonyl, methanesulfonyl, benzenesulfonyl, trifluoromethanesulfonyl, or dimethylsulfamoyl; X represents O, S or NR$_3$, wherein $R^3$ is hydrogen; $C_{1-6}$alkyl; methanesulfonyl; benzenesulfonyl; trifluoromethanesulfonyl; dimethylsulfamoyl; aryl$^2$carbonyl$C_{1-4}$alkyl; $C_{1-4}$alkyloxycarbonyl; $C_{1-4}$alkyl substituted with aryl$^2$ and optionally with hydroxy; or $C_{1-4}$alkylcarbonyl$C_{1-4}$alkyl substituted with aryl$^2$;

aryl$^1$ is phenyl; phenyl substituted with 1, 2 or 3 substituents each independently selected from halo, hydroxy, $C_{1-6}$alkyl, $C_{1-6}$alkyloxy, nitro, amino, cyano, and trifluoromethyl; pyridinyl; pyridinyl substituted with 1, 2 or 3 substituents each independently selected from halo, hydroxy, $C_{1-6}$alkyl, amino, and di$C_{1-4}$alkylamino; naphthyl; quinolinyl; 1,3-benzodioxolyl; furanyl; thienyl; or benzofuranyl; and aryl$^2$ is phenyl, or phenyl substituted with 1, 2 or 3 substituents each independently selected from halo, hydroxy, $C_{1-6}$alkyl, $C_{1-6}$alkyloxy, nitro, amino, cyano, and trifluoromethyl.

2. A compound as claimed in claim 1 wherein the bivalent radical

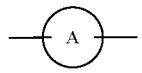

represents a radical of formula (a-1), (a-3) or (a-4) wherein $R^2$ represents hydrogen or hydroxy.

3. A compound as claimed in claim 1 wherein the bivalent radical -a$^1$=a$^2$—a$^3$=a$^4$- is of formula (b-1) wherein each hydrogen atom in said radicals (b-1) may optionally be replaced by halo, $C_{1-6}$alkyl, hydroxy, or $C_{1-6}$alkyloxy.

4. A compound as claimed in claim 1 wherein the bivalent radical -a$^1$=a$^2$—a$^3$=a$^4$- is of formula (b-2) wherein each hydrogen atom in said radicals (b-2) may optionally be replaced by halo, $C_{1-6}$alkyl, hydroxy, or $C_{1-6}$alkyloxy.

5. A compound as claimed in any of claims 1 to 4 wherein the $R^1$ represents hydrogen, $C_{1-6}$alkyl, phenylmethyl, or furanylmethyl.

6. A compound as claimed in claims 1 wherein X is NR$^3$, wherein $R^3$ is hydrogen, dimethylsulfamoyl, or $C_{1-4}$alkyl substituted with aryl$^2$.

7. A pharmaceutical composition comprising a pharmaceutically acceptable carrier and a therapeutically active amount of a compound as claimed in claim 1.

8. A process for preparing a compound as claimed in claim 1 a) an intermediate of formula (II), or a functional derivative thereof, is reacted with an intermediate of formula (III) in the presence of polyphosphoric acid (PPA) or phosphorus oxychloride (POCl$_3$), at a temperature ranging between room temperature and the reflux temperature of the reaction mixture, optionally said reaction may be performed in a reaction-inert solvent,

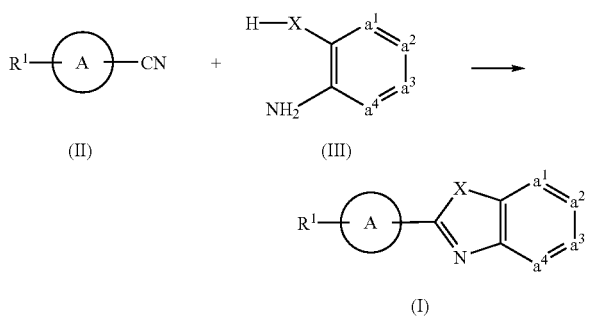

b) or, an intermediate of formula (IV), defined as a derivative of an intermediate of formula

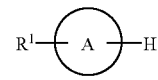

wherein two geminal hydrogen atoms are replaced by a carbonyl group, is reacted with an intermediate of formula (V), thereby yielding compounds of formula (I-a), defined as compounds of formula (I) wherein $R^2$ represents hydroxy,

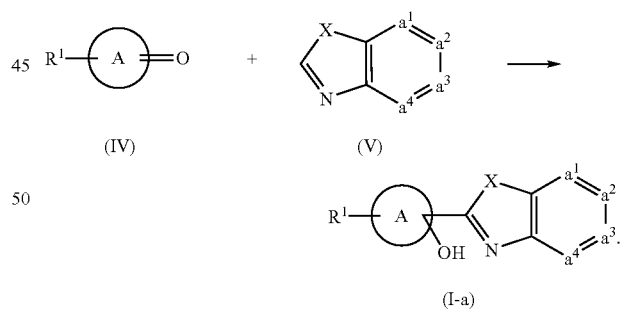

9. A method of treating conditions related to a hampered or impaired relaxation of the fundus comprising administering to a warm-blooded animal in need thereof an effective amount of a compound as claimed in claim 1.

* * * * *